United States Patent [19]

Boden et al.

[11] 4,452,730

[45] Jun. 5, 1984

[54] ALKYL-4-CYCLOOCTENYL CARBONATES AND USES THEREOF IN AUGMENTING OR ENHANCING THE AROMA OF PERFUME COMPOSITIONS, COLOGNES AND PERFUMED ARTICLES

[75] Inventors: Richard M. Boden, Ocean; Michael Licciardello, Farmingdale, both of N.J.

[73] Assignee: International Flavors & Fragrances Inc., New York, N.Y.

[21] Appl. No.: 496,649

[22] Filed: May 20, 1983

Related U.S. Application Data

[60] Division of Ser. No. 409,718, Aug. 19, 1982, Pat. No. 4,397,789, which is a continuation-in-part of Ser. No. 318,427, Nov. 15, 1981, abandoned.

[51] Int. Cl.[3] ........................... A61K 7/46; C11B 9/00

[52] U.S. Cl. ................................. 252/522 R; 260/463

[58] Field of Search ..................... 252/522 R; 260/463

[56] References Cited

U.S. PATENT DOCUMENTS 3,524,884 8/1970 Kretschmar ................ 252/522 R X 4,080,309 3/1978 Bruns et al. ..................... 252/522 R

*Primary Examiner*—Helen M. S. Sneed

*Attorney, Agent, or Firm*—Arthur L. Liberman

[57] ABSTRACT

Described are the 4-cyclooctenyl alkyl carbonates defined according to the structure:

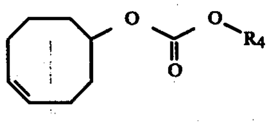

wherein $R_4$ is methyl or ethyl, reaction products including a major proportion of said 4-cyclooctenyl alkylcarbonates and a minor proportion of bicyclooctanyl carbonates having the structures:

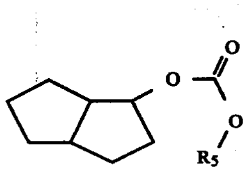

wherein $R_5$ is methyl or ethyl, and uses thereof in augmenting or enhancing the aroma of perfume compositions, colognes and perfumed articles such as solid or liquid anionic, cationic, nonionic or Zwitterionic detergents, fabric softeners, fabric softener articles, hair sprays, shampoos, bath oils and perfumed polymers.

4 Claims, 14 Drawing Figures

FIG. I

GLC PROFILE FOR FRACTION 7 OF EXAMPLE I.

NMR SPECTRUM FOR FRACTION 5 OF EXAMPLE I.

IR SPECTRUM FOR FRACTION 5 OF EXAMPLE I.

GLC PROFILE FOR EXAMPLE II.

GLC PROFILE FOR EXAMPLE II, FRACTION 5.

NMR SPECTRUM FOR FRACTION 13, EXAMPLE II.

IR SPECTRUM FOR FRACTION 13 OF EXAMPLE II.

GLC PROFILE FOR FRACTION 7 OF EXAMPLE II.

NMR SPECTRUM FOR FRACTION 7 OF EXAMPLE II.

IR SPECTRUM FOR FRACTION 7 OF EXAMPLE II.

GLC PROFILE FOR EXAMPLE III.

GLC PROFILE FOR FRACTION 6 OF EXAMPLE III.

IR SPECTRUM FOR BULKED FRACTIONS 9-12 OF EXAMPLE III.

NMR SPECTRUM FOR BULKED FRACTIONS 9-12 OF EXAMPLE III

ALKYL-4-CYCLOOCTENYL CARBONATES AND USES THEREOF IN AUGMENTING OR ENHANCING THE AROMA OF PERFUME COMPOSITIONS, COLOGNES AND PERFUMED ARTICLES

This is a divisional of application Ser. No. 409,718, filed Aug. 19, 1982, now U.S. Pat. No. 4,397,789, which, in turn, is a continuation-in-part of application for U.S. Patent, Ser. No. 318,427 filed on Nov. 15, 1981, now abandoned.

BACKGROUND OF THE INVENTION

This invention relates to 4-cyclooctenyl alkyl carbonates defined according to the structure:

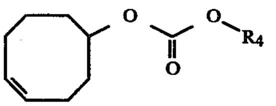

wherein $R_4$ is methyl or ethyl and mixtures containing high proportions of said 4-cyclooctenyl alkyl carbonates and minor proportions of bicyclooctanyl carbonates having the structure:

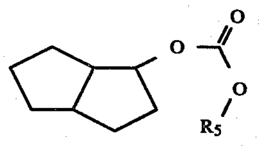

wherein $R_5$ is methyl or ethyl and uses of such mixtures and said 4-cyclooctenyl alkyl carbonate in augmenting or enhancing the aroma of perfume compositions, colognes and perfumed articles.

Materials which can provide minty, strawberry-like, herbal, sweet, intense, violet-like, green, cucumber-like, pear-like and banana-like aroma nuances with tagette-like and birch tar-like undertones are highly desirable in the art of perfumery. Many of the natural substances which provide such fragrance nuances and contribute the desired nuances to perfumery compositions are high in cost, vary in quality from one batch to another and/or are generally subject to the usual variations of natural products.

The prior art contains a large number of teachings regarding the use of organic carbonates in augmenting or enhancing the aroma of perfumes. Thus, U.S. Pat. No. 4,033,993 discloses the use of organic carbonates defined according to the structure:

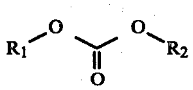

wherein $R_1$ is a moiety having from 8 to 12 carbon atoms selected from the group consisting of alkylcyclohexyl, alkenylcyclohexyl, alkynylcyclohexyl and cycloalkyl and $R_2$ is a moiety selected from the group consisting of alkyl having from 1 to 5 carbon atoms, alkenyl having from 2 to 5 carbon atoms and alkynyl having from 2 to 5 carbon atoms. U.S. Pat. No. 4,033,993 describes, for example, methyl-1-ethynycyclohexyl carbonate having a fruity, herbal complex odor and distinct fragrance of dill. In addition, U.S. Pat. No. 4,033,993 describes methyl cyclooctyl carbonate as having an herbal, natural and complex fragrance which is distinguished by a strong and long clinging flowery jasmine scent and further indicates its use in jasmine perfume compositions. U.S. Pat. No. 4,033,993 describes the preparation of the compounds defined according to the structure:

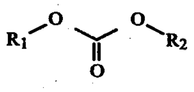

according to the reaction:

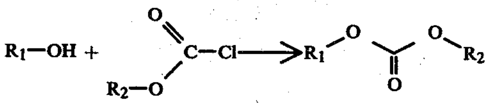

wherein $R_1$ and $R_2$ are defined as above.

In addition, U.S. Pat. No. 4,080,309 describes the perfume use of the carbonates defined according to the structure:

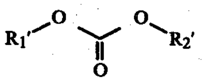

wherein $R_1'$ is a moiety having from 8 to 12 carbon atoms selected from the group consisting of alkylcyclohexyl, alkenylcyclohexyl, alkynylcyclohexyl and cycloalkyl and $R_2'$ is a moiety selected from the group consisting of alkyl having from 1 to 5 carbon atoms, alkenyl having from 2 to 5 carbon atoms and alkynyl having from 2 to 5 carbon atoms. Described in U.S. Pat. No. 4,080,309 are also such compounds as methyl cyclooctyl carbonate and the use thereof in jasmine perfume formulations. As is the case in U.S. Pat. No. 4,033,993, the carbonates of 4,080,309 are indicated to be prepared according to the reaction:

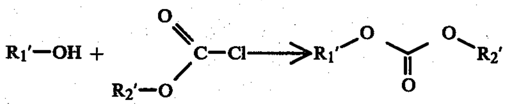

4-Cyclooctenyl formate having the structure:

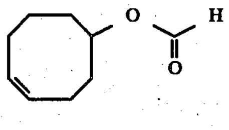

a precursor of the 4-cyclooctenyl alkyl carbonates of our invention, is indicated to be produced by reaction of 1,5-cyclooctadiene with formic acid in German Offenlegungsschrift 3,037,093 published on Nov. 12, 1981, the specification for which is incorporated by reference herein. Said German Offenlegungsschrift is abstracted in Chem. Abstracts, Volume 96, 68448q.

Nothing in the prior art, however, discloses the 4-cyclooctenyl alkyl carbonates of our invention and nothing discloses such 4-cyclooctenyl alkyl carbonates as having the specific fragrance nuances and fragrance utilities as set forth infra.

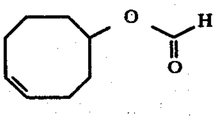
(major proportion)

and

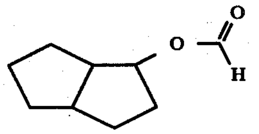
(minor proportion)

Figure 2:
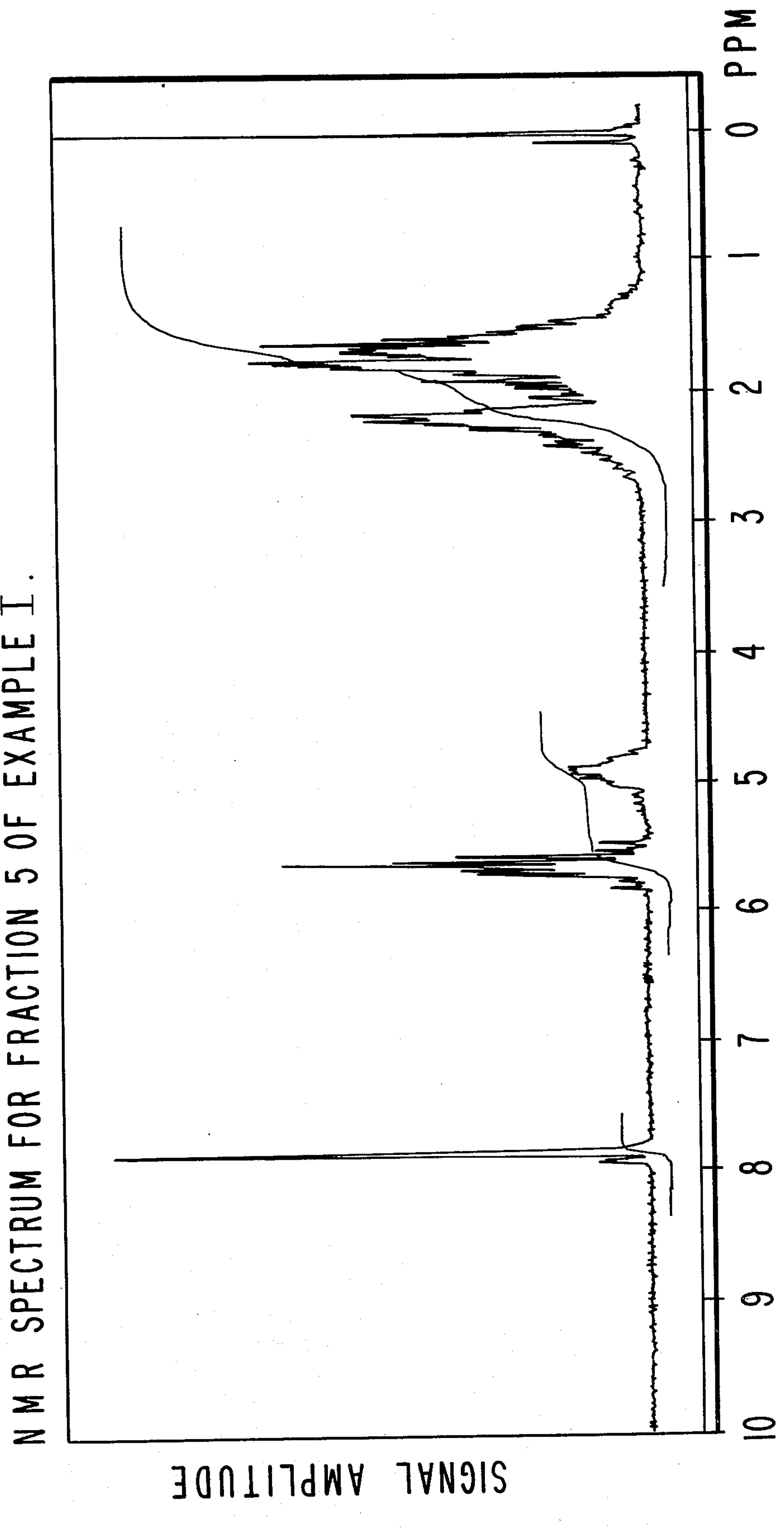

FIG. 2 is the NMR spectrum for fraction 5 of the distillation product of the reaction product of Example I contaning the compounds having the structures:

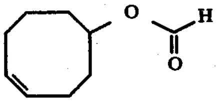
(major proportion)

and

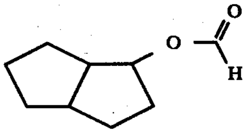
(minor proportion)

(conditions: $CFCl_3$ Solvent; 100 MHz Field Strength).

Figure 3:
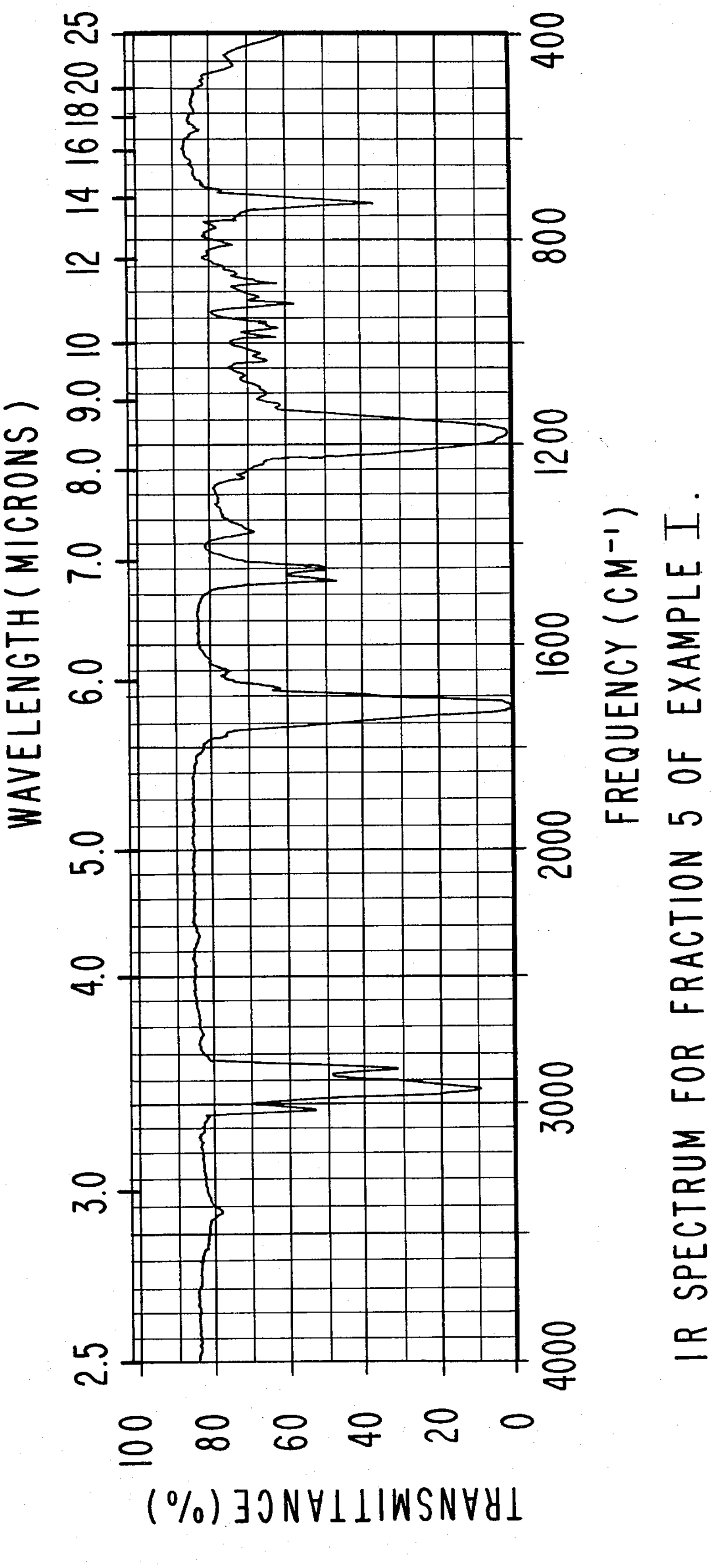

FIG. 3 is the infra-red spectrum for fraction 5 of the distillation product of the reaction product of Example I containing the compounds having the structures:

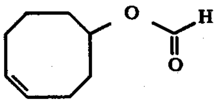
(major proportion)

and

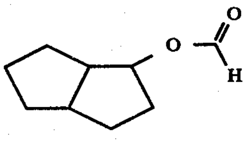
(minor proportion)

Figure 4:
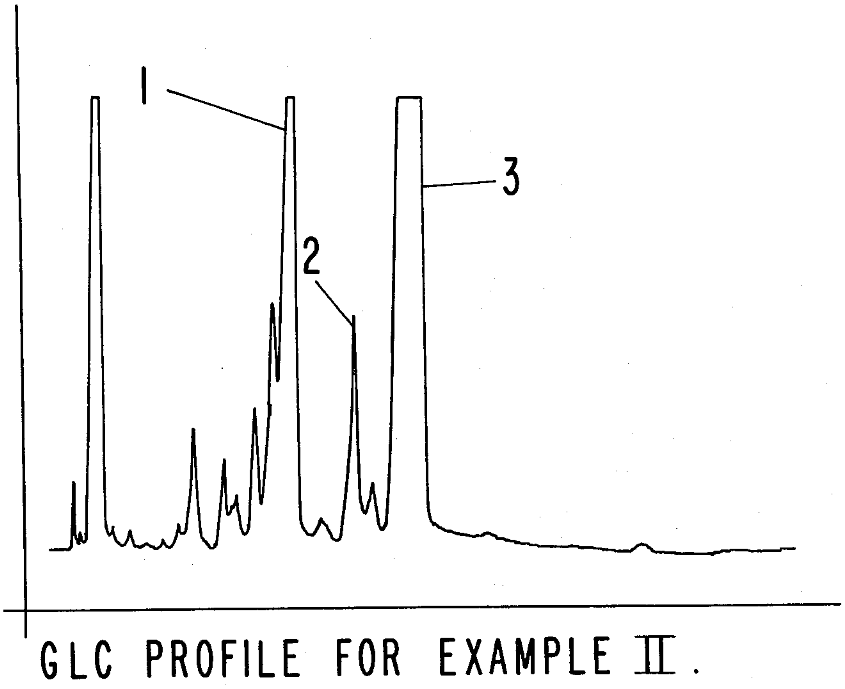

FIG. 4 is the GLC profile for the reaction product of Example II containing the compounds having the structures:

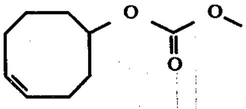
(major proportion)

and

-continued

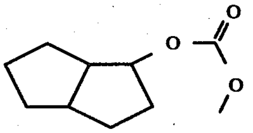
(minor proportion)

Figure 5:
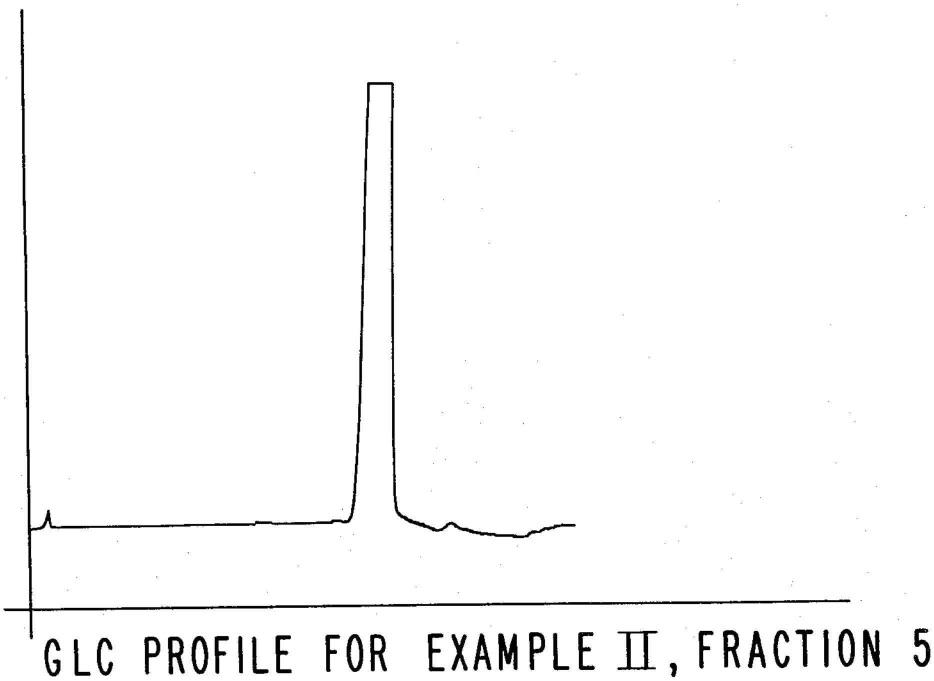

FIG. 5 is the GLC profile for fraction 13 of the distillation product of the reaction product of Example II containing the compounds having the structures:

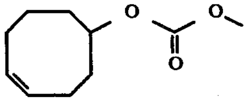
(major proportion)

and

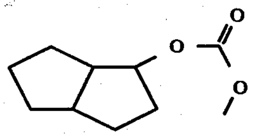
(minor proportion)

Figure 6:
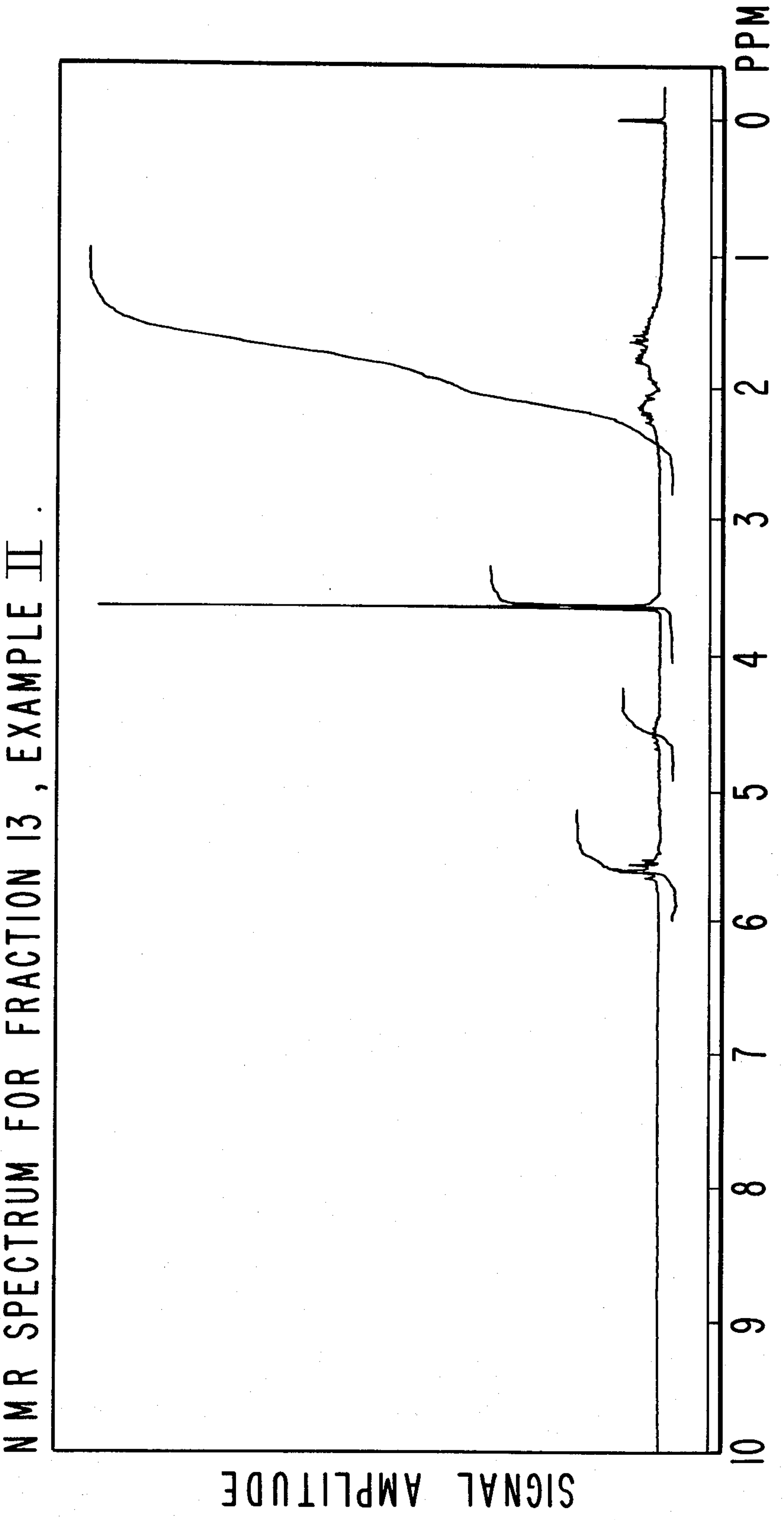

FIG. 6 is the NMR spectrum for fraction 13 of the distillation product of the reaction product of Example II containing the compounds having the structures:

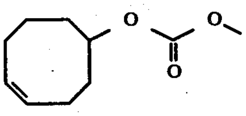
(major proportion)

and

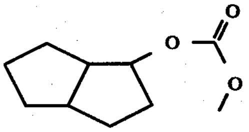
(minor proportion)

Figure 7:
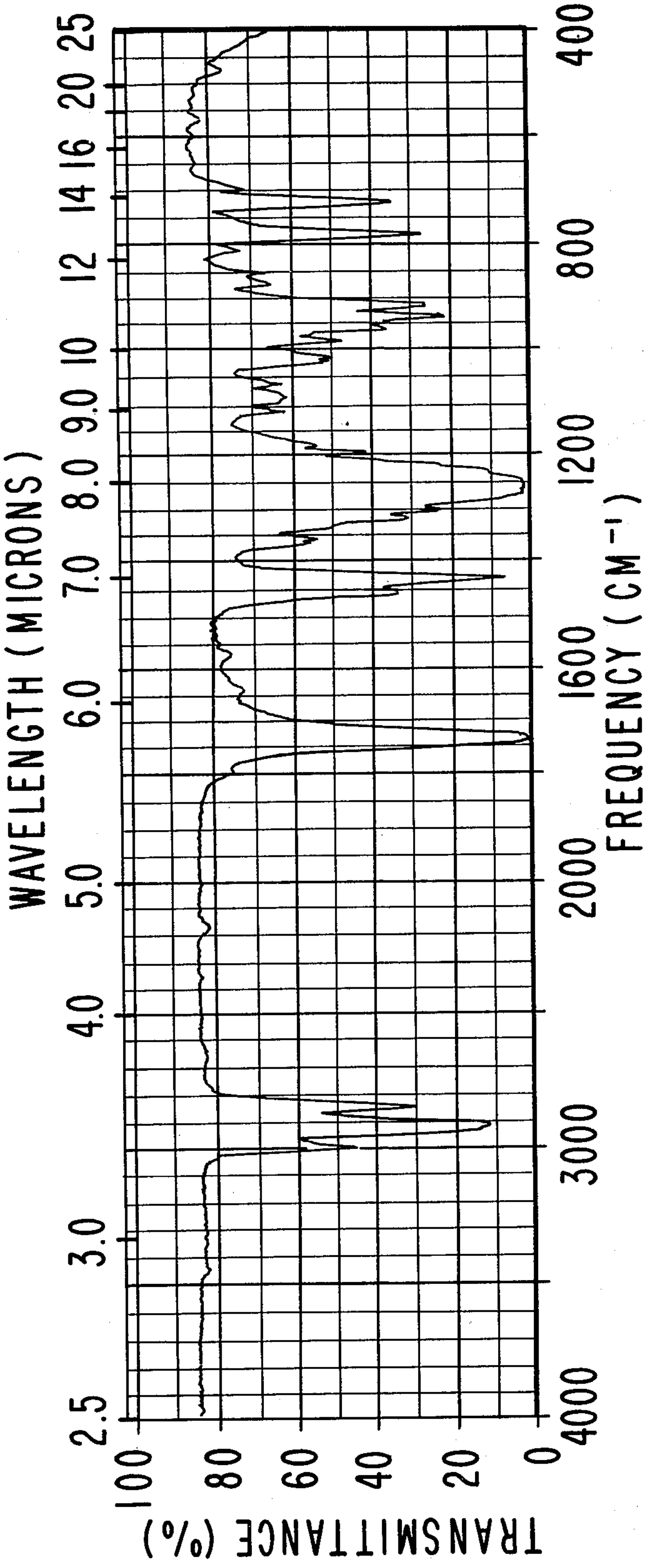

FIG. 7 is the infra-red spectrum for fraction 13 of the distillation product of the reaction product of Example II containing the compounds having the structures:

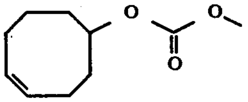
(major proportion)

and

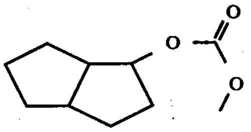
(minor proportion)

Figure 8:
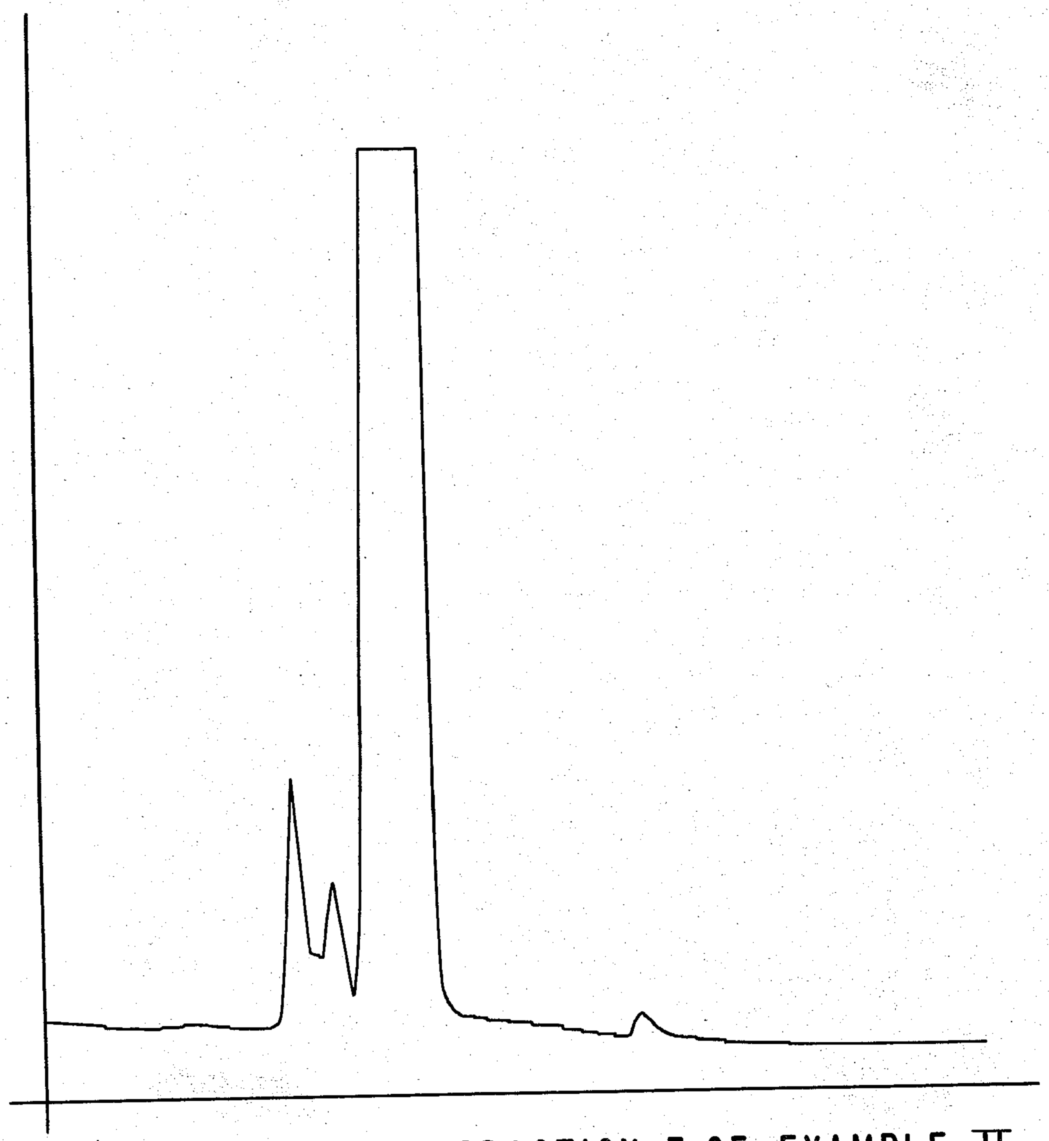

FIG. 8 is the GLC profile for fraction 7 of the distillation product of the reaction product of Example II containing the compound having the structure:

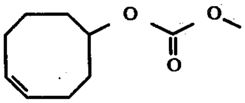

in major proportion and the compound having the structure:

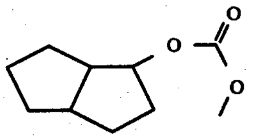

in minor proportion.

Figure 9:
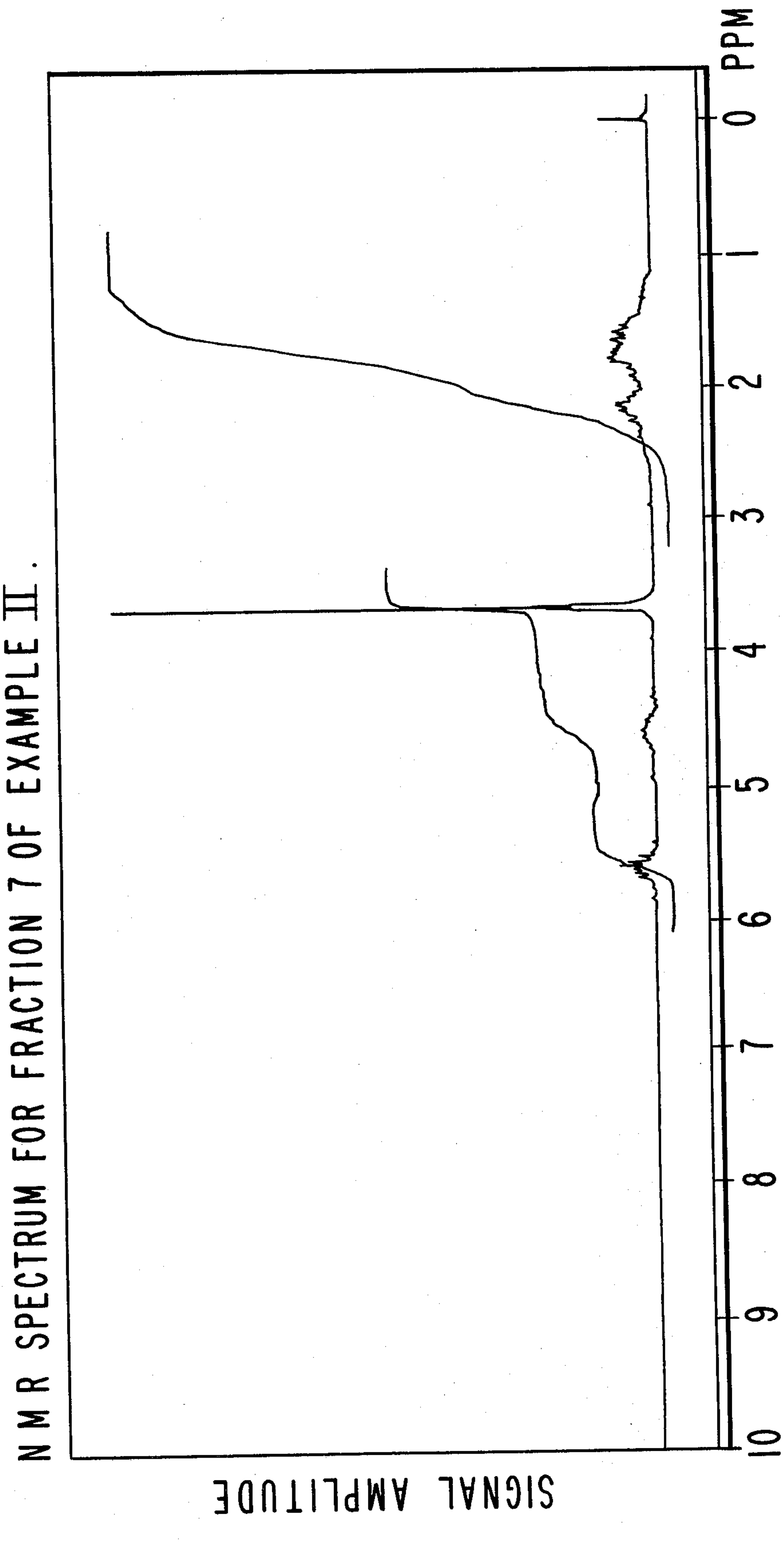

FIG. 9 is the NMR spectrum for fraction 7 of the distillation product of the reaction product of Example II containing the compound having the structure:

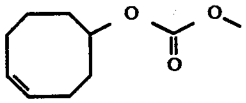

in major proportion and the compound having the structure:

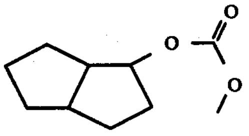

in minor proportion (Solvent: $CFCl_3$; Field Strength: 100 MHz).

Figure 10:
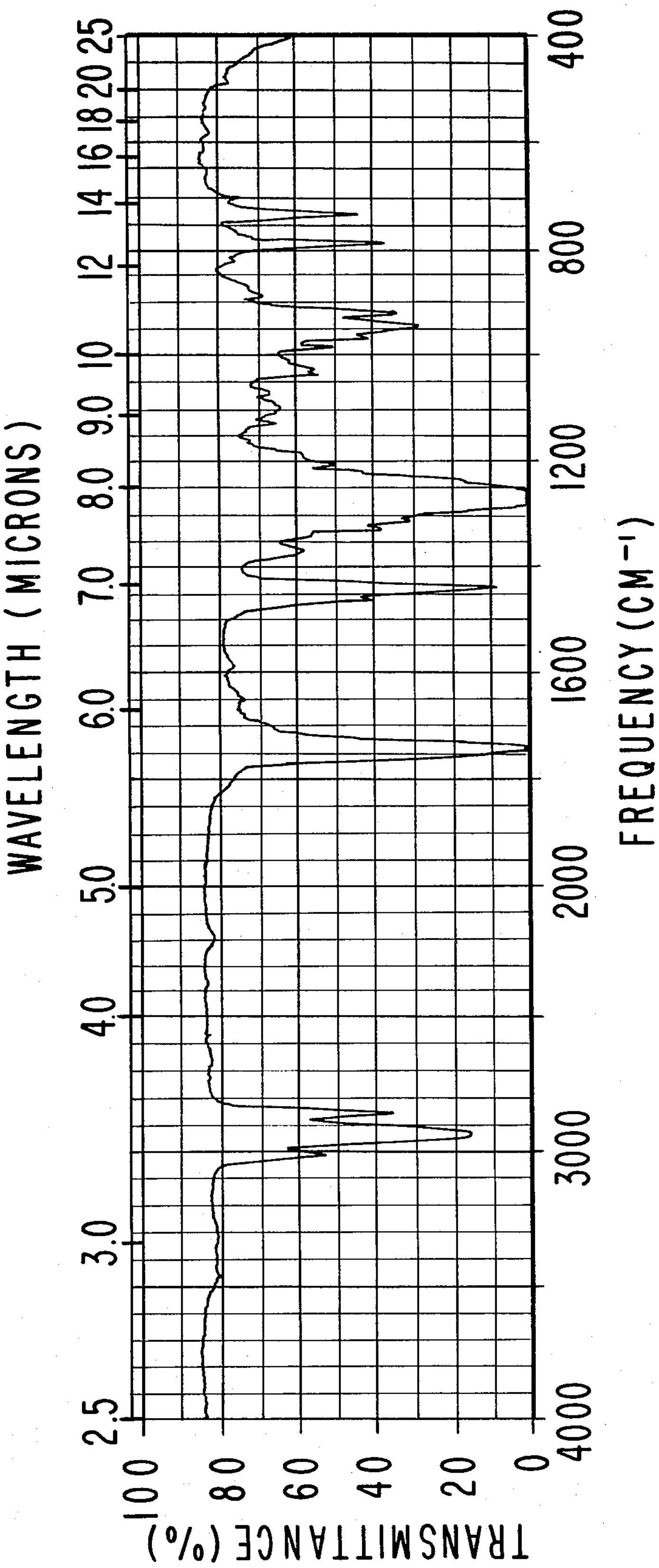

FIG. 10 is the infra-red spectrum for fraction 7 of the distillation product of the reaction product of Example II containing the compound having the structure:

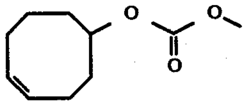

in major proportion and the compound having the structure:

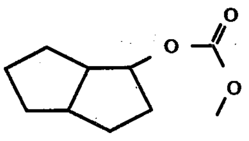

in minor proportion (ratio of compound having the structure:

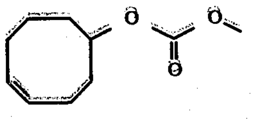

compound having the structure:

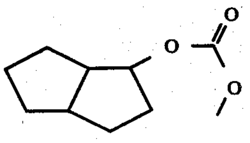

being 77:19).

Figure 11:
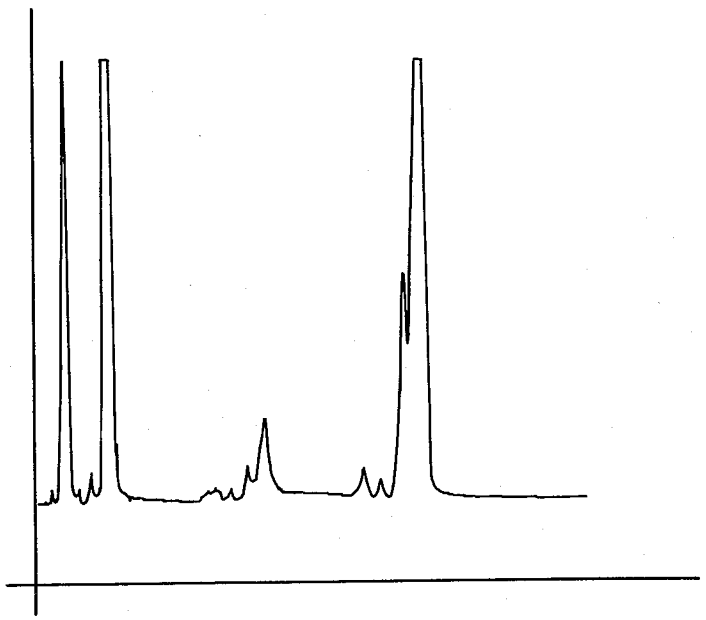

FIG. 11 is the GLC profile for the reaction product of Example III containing the compounds having the structures:

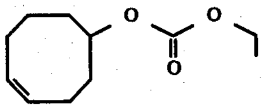

(major proportion)

and

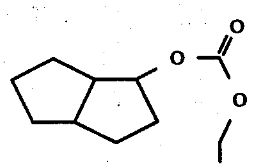

(minor proportion)

(conditions: SE-30 column, 6'×¼", programmed at 100°-220° C. at 8° C. per minute).

Figure 12:
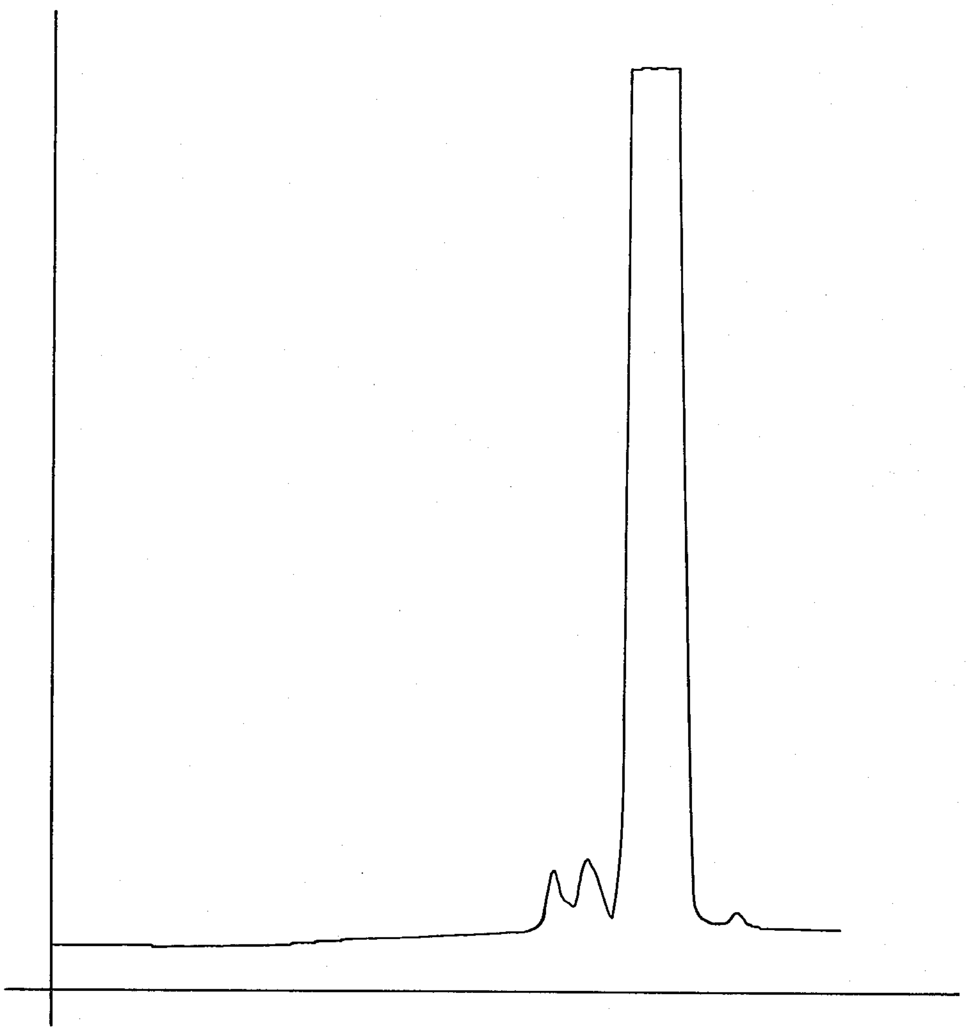

FIG. 12 is the GLC profile for fraction 6 of the distillation product of the reaction product of Example III containing the compounds having the structures:

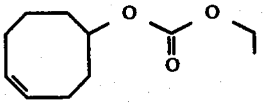

(major proportion)

and

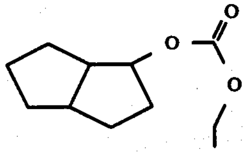

(minor proportion)

Figure 13:
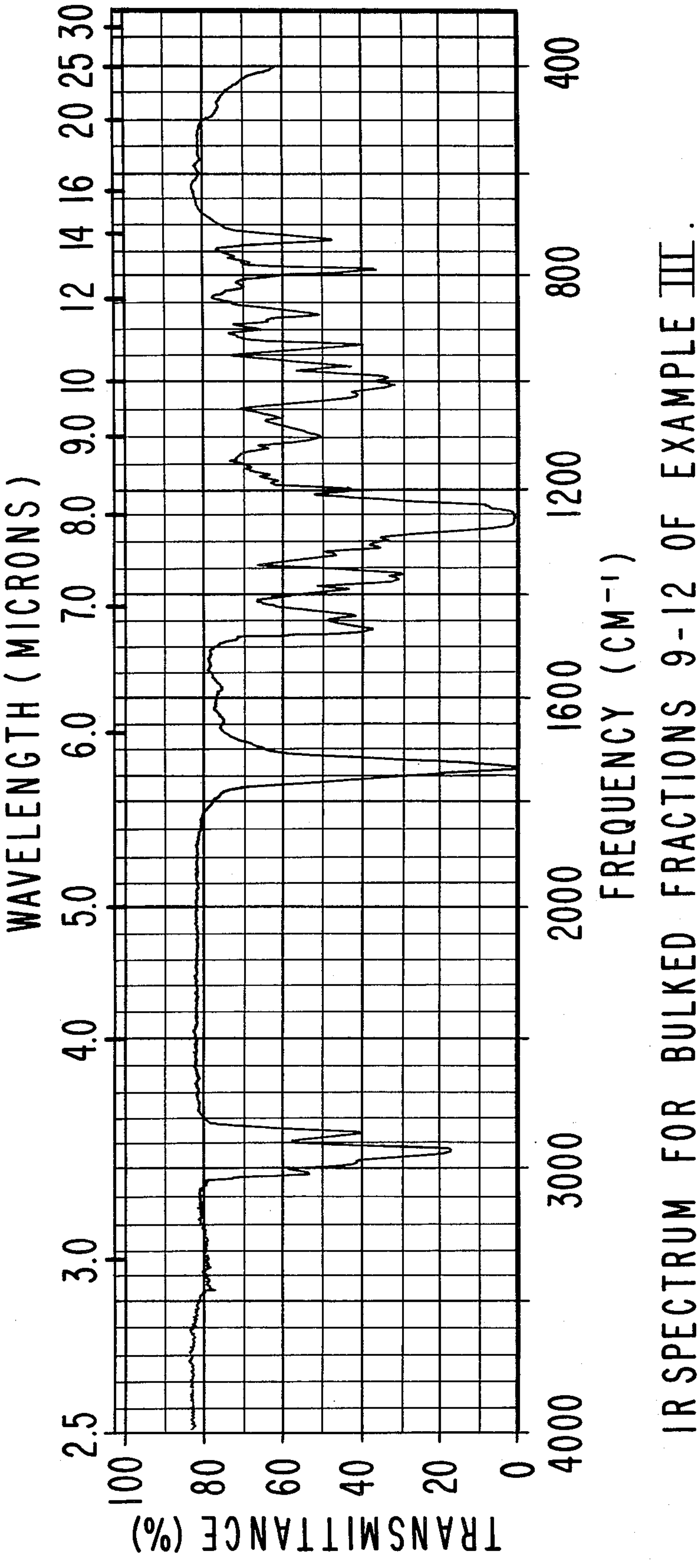

FIG. 13 is the infra-red spectrum for bulked fractions 9-12 of the distillation product of the reaction product of Example III containing the compounds having the structures:

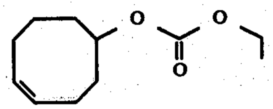

(major proportion)

and

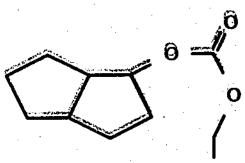

(minor proportion)

Figure 14:
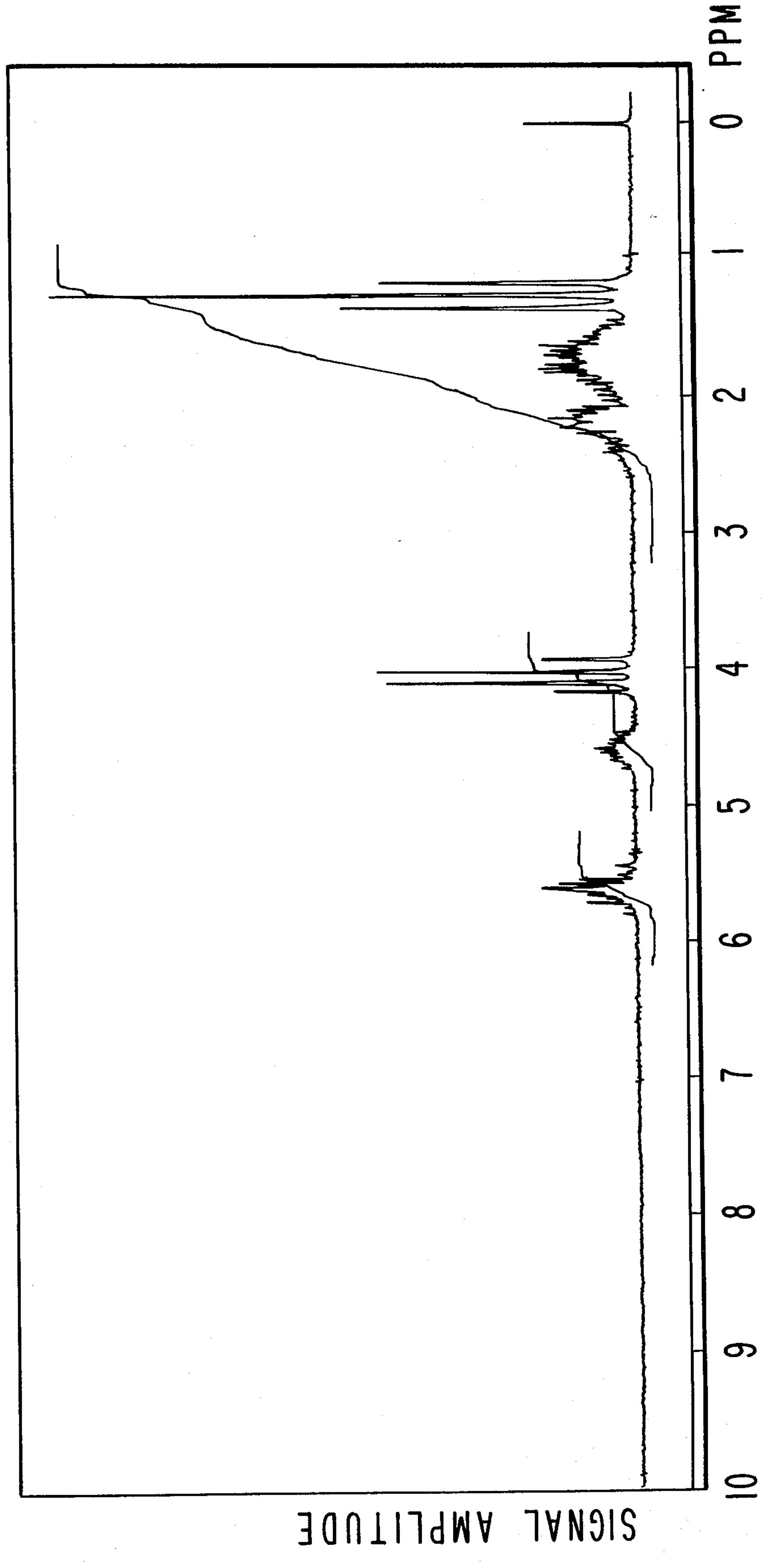

FIG. 14 is the NMR spectrum for bulked fractions 9-12 of the distillation product of the reaction product of Example III containing the compounds having the structures:

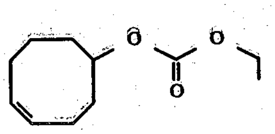

(major proportion)

and

-continued

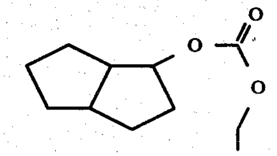

(minor proportion)

(conditions: $CFCl_3$ Solvent; 100 MHz Field Strength).

DETAILED DESCRIPTION OF FIG. 4

FIG. 4 is the GLC profile for the reaction product of Example II wherein the reaction carried out is as follows:

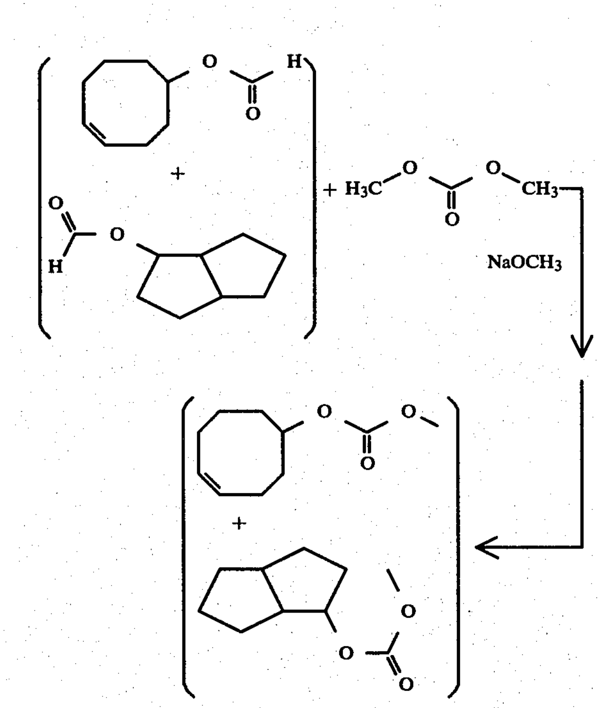

Peak 1 of this GLC profile is the peak signifying methyl alcohol. Peak 2 of this GLC profile is the peak signifying 4-cyclooctenyl formate having the structure:

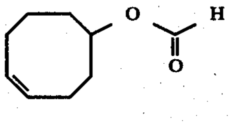

The peak signified by the numeral "3" is the peak representing methyl-4-cyclooctenyl carbonate defined according to the structure:

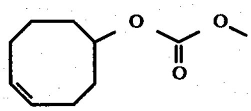

THE INVENTION

The present invention provides compounds defined according to the structure:

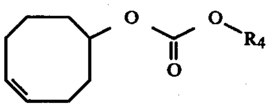

wherein $R_4$ represents methyl or ethyl. The present invention also provides an economically efficient process for synthesizing the compounds having the structure:

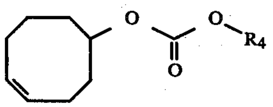

by reacting a dialkyl carbonate defined according to the structure:

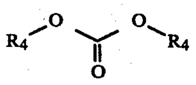

with 4-cyclooctenyl formate in the presence of an alkali metal alkoxide according to the reaction:

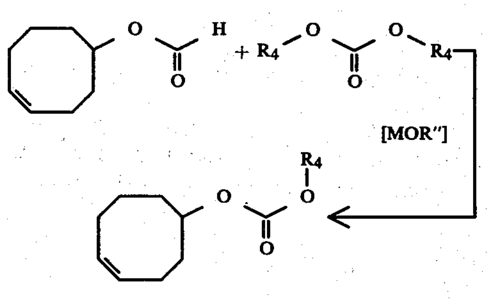

wherein $R_4$ is ethyl or methyl and wherein M represents alkali metal such as sodium, potassium or lithium and R" represents lower alkyl such as methyl, ethyl, n-propyl, isopropyl, n-butyl, secondary butyl or t-butyl.

Actually, the cyclooctenyl formate which is formed from 1,5-cyclooctadiene by reaction of the 1,5-cyclooctadiene with formic acid, contains a small amount of bicyclooctanyl formate defined according to the structure:

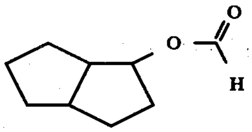

Thus, the sequence of reactions that takes place in order to produce a commercial mixture containing a preponderant proportion of 4-cyclooctenyl alkyl carbonate defined according to the structure:

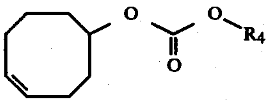

but also contains a minor proportion of carbonate defined according to the structure:

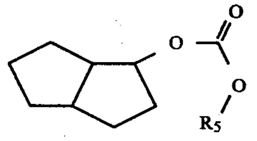

starts by first reacting 1,5-cyclooctadiene with formic acid yielding the mixture of bicyclooctanyl formate having the structure:

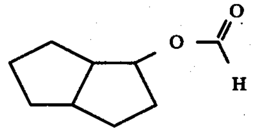

and 4-cyclooctenyl formate having the structure:

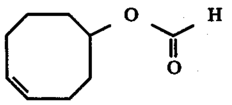

according to the reaction:

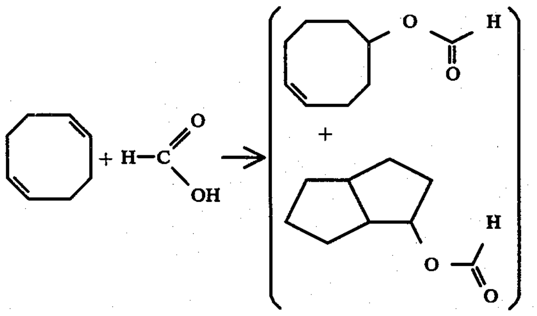

The resulting mixture of compounds is then reacted with either diethyl carbonate or dimethyl carbonate defined according to the structure:

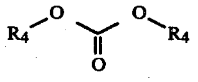

wherein $R_4$ is methyl or ethyl thereby forming the mixture of carbonates according to the reaction:

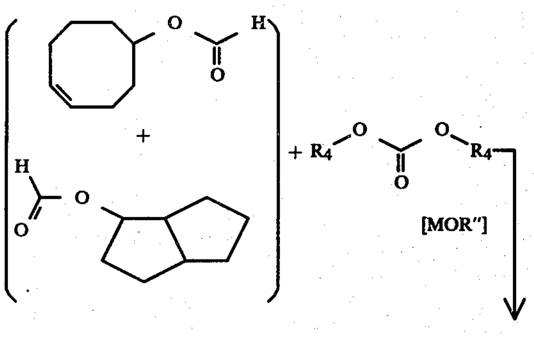

-continued

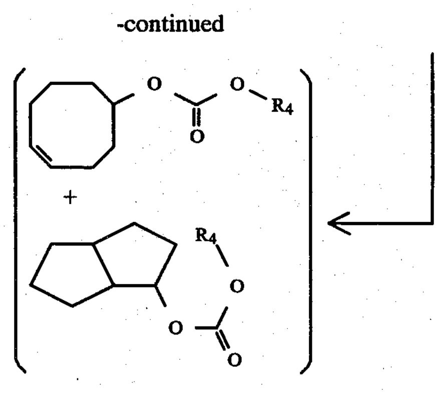

wherein $R_4$, M and R″ are defined supra.

The 4-cyclooctenyl alkyl carbonates of our invention are commercially mixtures of "endo" and "exo" molecules defined according to the structures:

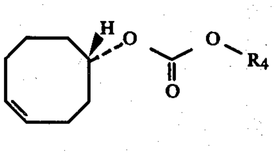

and

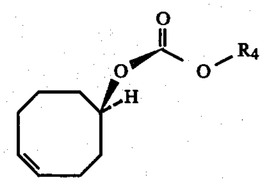

However, these molecules may be separated using commercial chromatographic techniques, if desired.

At the end of the reaction, the reaction mixture which consists of a preponderant amount of 4-cyclooctenyl alkyl carbonate defined according to the structure:

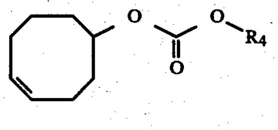

and bicyclooctanyl alkyl carbonate having the structure

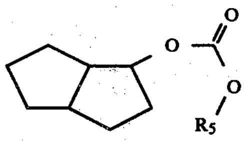

may be used "as is" or the bicyclooctanyl alkyl carbonate may be separated from the 4-cyclooctenyl alkyl carbonate by commercial chromatographic techniques.

The present invention also provides processes for using the compounds defined according to the generic structure:

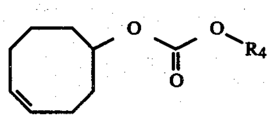

or the commercial mixtures containing such compounds and minor proportions of bicyclooctanyl alkyl carbonates having the structure:

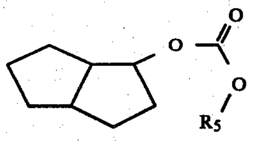

wherein $R_5$ is ethyl or methyl for their organoleptic properties in augmenting or enhancing the organoleptic properties of consumable materials, that is, the aroma of perfumes, colognes and perfumed articles (such as perfumed polymers, solid or liquid cationic, anionic, nonionic or zwitterionic detergents, soaps, fabric softener compositions, drier-added fabric softener articles such as BOUNCE ®, the registered trademark of Proctor & Gamble Company of Cincinnati, Ohio, fabric brighteners, cosmetic powders, bath preparations, hair preparations such as hair sprays and shampoos).

As stated supra, the 4-cyclooctenyl alkyl carbonates of our invention may be prepared by first reacting 1,5-cyclooctadiene with formic acid thereby producing a mixture containing a preponderant amount of 4-cyclooctenyl formate and a minor quantity of bicyclooctanyl formate defined according to the structure:

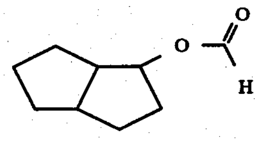

according to the reaction:

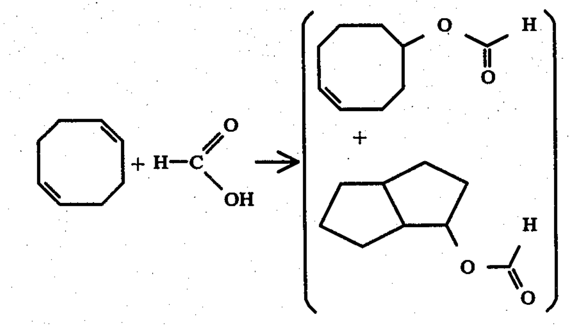

This reaction is carried out using a molar excess of the formic acid (with a mole ratio range of formic acid:1,5-cyclooctadiene being from about 2:1 up to about 7:1). The reaction temperature is conveniently at reflux, e.g. 95°-110° C. at atmospheric pressure. Pressures higher than atmospheric may be used with consequently higher temperatures of reaction and shorter times of reaction. However, it is most convenient to carry out the reaction at atmospheric pressure and at a temperature of between about 95° and about 105° C. At the end of the reaction, the reaction mass is "worked-up" using standard extraction techniques and fractional distillation techniques whereby the resulting 4-cyclooctenyl formate in admixture with a minor quantity of bicyclooctanyl formate is produced for subsequent reaction with the dialkyl carbonate.

The 4-cyclooctenyl alkyl carbonates of our invention may be prepared from the 4-cyclooctenyl formate by reacting the 4-cyclooctenyl formate (taken alone or in admixture with the bicyclooctanyl formate in minor quantity) with a dialkyl carbonate according to either the reaction:

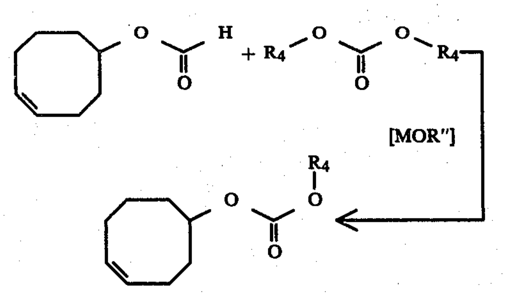

or the reaction:

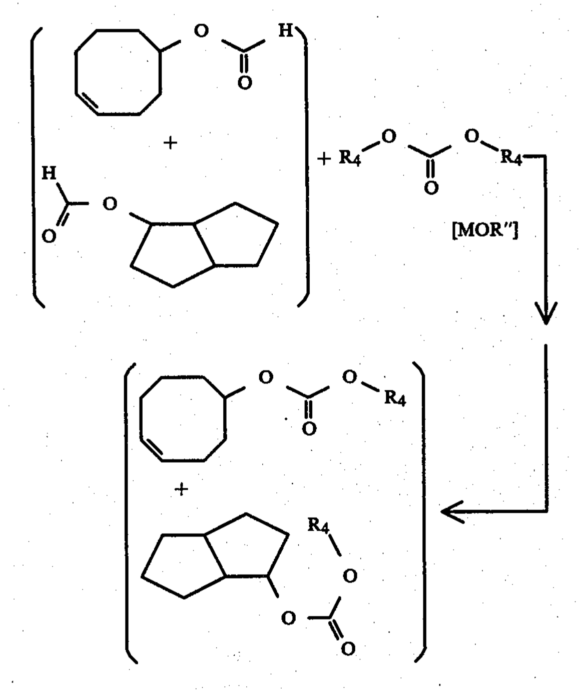

wherein $R_4$ represents ethyl or methyl, M represents sodium, potassium or lithium and R" represents lower alkyl, e.g. methyl, ethyl, n-propyl, isopropyl, n-butyl, isobutyl or t-butyl. Thus, the reaction takes place in the presence of an alkali metal alkoxide such as sodium methoxide, sodium ethoxide, sodium t-butoxide, potassium methoxide, potassium ethoxide and potassium t-butoxide. The reaction between the formate ester and the dialkyl carbonate takes place in the absence of any additional solvent. The mole ratio range of dialkyl carbonate:formate ester may vary from 3 moles dialkyl carbonate:0.5 moles formate ester down to 1 mole dialkyl carbonate:1 mole formate ester. It is preferred that the mole ratio of dialkyl carbonate:formate ester be about 2:1. The molar concentration in the reaction mass of the alkali metal alkoxide catalyst may vary from about 0.005 up to about 0.01 with a mole ratio of about 0.05 being preferred.

The reaction temperature range may vary from about 50° C. up to about 100° C. and the reaction pressure may vary from atmospheric pressure up to about 10 atmospheres. Higher temperature of reaction necessitates higher pressure over the reaction mass in order to prevent the reaction product from evaporating therefrom, but higher reaction temperature gives rise to shorter times of reaction to reach the desired conversion.

At the end of the reaction, the reaction product is purified according to standard procedures such as fractional distillation and, if necessary, chromatographic separation as by high pressure liquid chromatography or GLC (vapor phase chromatography).

Chromatographic apparatus useful in conjunction with carrying out the foregoing separation is disclosed and claimed in U.S. Pat. No. 4,230,464, the disclosure of which is incorporated by reference herein.

Examples of reaction products prepared in accordance with the process of our invention and their organoleptic properties are as follows:

TABLE I

| Reaction Product | Aroma Properties |
| --- | --- |
| Mixture of compounds having the structures: 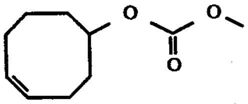 (major proportion) and 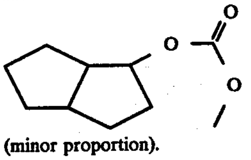 (minor proportion). | A sweet, fruity (pear, banana), violet-like and green cucumber aroma profile. |
| Mixture of compounds having the structures: 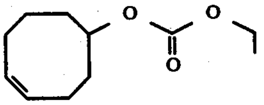 (major proportion) and 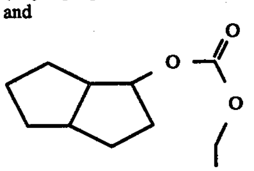 (minor proportion). | A minty, strawberry-like aroma with tagette-like nuances on dry-out and a minty, strawberry-like, herbal aroma with tagette-like and birch tar-like undertones in general. |

The 4-cyclooctenyl alkyl carbonates of our invention can be used to contribute minty, strawberry-like, herbal, sweet, intense violet, green, cucumber-like, pear-like and banana-like aroma nuances with tagette-like and birch tar-like undertones to perfume compositions, perfumed articles such as solid or liquid anionic, cationic, nonionic or zwitterionic detergents, perfumed polymers, fabric softener compositions, fabric softener articles, optical brighteners, fabric conditioners, hair preparations, shampoos and hair sprays. As olfactory agents, the 4-cyclooctenyl alkyl carbonates of our invention can be formulated into or used as components of a "perfume composition".

The term "perfume composition" is used herein to mean a mixture of organic compounds including, for example, alcohols, aldehydes, ketones, nitriles, ethers, lactones, esters other than the carbonates of our invention, and frequently hydrocarbons which are admixed so that the combined odors of the individual components produce a pleasant or desired fragrance. Such perfume compositions usually contain: (a) the main note or the "bouquet" or foundation stone of the composition; (b) modifiers which round off and accompany the main note; (c) fixatives which include odorous substances which lend a particular note to the perfume throughout all stages of evaporation and substances which retard evaporation and (d) top notes which are usually low-boiling, fresh-smelling materials.

In perfume compositions, the individual component will contribute its particular olfactory characteristics, but the overall effect of the perfume composition will be the sum of each of the effects of each of the ingredients. Thus, the individual compounds of this invention or mixtures thereof can be used to alter the aroma characteristics of the perfume composition, for example, by highlighting or moderating the olfactory reaction contributed by another ingredient in the composition.

The amount of 4-cyclooctenyl alkyl carbonate(s) of our invention which will be effective in perfume compositions depends upon many factors including the other ingredients, their amounts and the effects which are desired. It has been found that perfume compositions containing as little as 0.1% of the 4-cyclooctenyl alkyl carbonate(s) of our invention or even less and perfume compositions containing as much as 70% of one or more of the 4-cyclooctenyl alkyl carbonate(s) of our invention can be used to impart interesting, minty, strawberry-like, herbal, sweet, intense violet, green, cucumber-like, pear-like and banana-like nuances with tagette-like and birch tar-like undertones to perfumed articles, perfume compositions and colognes. Such perfumed articles include fabric softener compositions, drier-added fabric softener articles, cosmetic powders, talcs, solid or liquid anionic, cationic, nonionic or zwitterionic detergents and perfumed polymers. The amount employed can range up to 70% and will depend on considerations of cost, nature of the end product and the effect desired on the finished product and particular fragrance sought.

Thus, one or more of the 4-cyclooctenyl alkyl carbonate(s) of our invention can be used alone or in a perfume composition as an olfactory component, in solid or liquid anionic, cationic, nonionic or zwitterionic detergents (including soaps) perfumed polymers (those which are microporous and those which are macroporous and contain particulate absorbent fillers such as talc), space odorants and deodorants; perfumes, colognes, tiolet waters, bath salts, hair preparations such as lacquers, brilliantines, pomades and shampoos; cosmetic preparations such as creams, deodorants, hand lotions and sun screens; powders such as talcs, dusting powders, face powders and the like.

When used as an olfactory component of a perfumed article such as a microporous polymer or a macroporous polymer containing an absorbent filler or such as a solid or liquid cationic, anionic, nonionic or zwitterionic detergent or of a cosmetic powder, as little as 0.01% of one or more of the 4-cyclooctenyl alkyl carbonate(s) of our invention will suffice to provide interesting minty, strawberry-like, herbal, sweet, intense violet, green, cucumber-like, pear-like and banana-like aromas with tagette-like and birch tar-like undertones. Generally, no more than 0.8% of one or more of the 4-cyclooctenyl alkyl carbonate(s) of our invention is required.

In addition, the perfume compositions of our invention can contain a vehicle or carrier for the 4-cyclooctenyl alkyl carbonate(s) of our invention alone or with other ingredients. The vehicle can be a liquid such as an alcohol such as ethanol, a glycol such as propylene glycol or the like. The carrier can be an absorbent solid such as a gum (e.g. xanthan gum or gum arabic) or components for encapsulating the composition as by coacervation (gelatin or using a urea formaldehyde prepolymer to form a polymeric shell around a liquid perfume center).

The following Example I sets forth a process for preparing the cyclooctenyl formate precursor used in carrying out the process for preparing the cyclooctenyl alkyl carbonates of our invention. The following Examples II and III set forth processes for preparing the 4-cyclooctenyl alkyl carbonates of our invention. The following Examples IV et seq. represent methods for using the 4-cyclooctenyl alkyl carbonates of our invention for their organoleptic properties.

Unless otherwise indicated, all parts and percentages are by weight.

EXAMPLE I

MIXTURE CONTAINING PREPONDERANT AMOUNT OF 4-CYCLOOCTENYL FORMATE

Reaction:

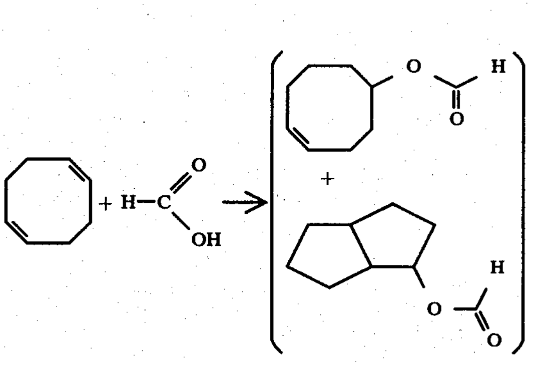

Into a 12-liter reaction flask equipped with heating mantle, stirrer, reflux condenser, addition funnel, thermometer and nitrogen blanket apparatus, is placed 7 kilograms (153 moles) of 90% formic acid. The formic acid is heated to reflux. During refluxing and over a period of 5.5 hours, while maintaining the temperature at 98°-100° C., 1,5-cyclooctadiene (3 kilograms; 27 moles) is added to the formic acid. The resulting mixture is refluxed at 98° C. for an additional 7.5 hours.

At the end of the 7.5 hour period, the reaction mass is transferred to a separatory funnel and 3 liters of toluene is added. The aqueous phase is separated from the organic phase and the organic phase is washed with two 5-liter portions of water followed by one 5-liter portion of 5% sodium carbonate and then one 5-liter portion of water again. The resulting organic phase is then dried over anhydrous magnesium sulfate and distilled on a 2" Splash column yielding the following fractions:

| Fraction Number | Vapor Temp. (°C.) | Liquid Temp. (°C.) | Vacuum mm/Hg. | % of 4-cyclo-octenyl formate |
|---|---|---|---|---|
| 1 | 45/51 | 50/67 | 20/6 | |
| 2 | 70 | 75 | 6 | 18.8 |
| 3 | 77 | 84 | 4 | 46.6 |
| 4 | 78 | 84 | 4 | 63.0 |
| 5 | 79 | 85 | 3 | 79.0 |
| 6 | 78 | 85 | 3 | 85.0 |

-continued

| Fraction Number | Vapor Temp. (°C.) | Liquid Temp. (°C.) | Vacuum mm/Hg. | % of 4-cyclo-octenyl formate |
|---|---|---|---|---|
| 7 | 80 | 85 | 3 | 88.0 |
| 8 | 81 | 91 | 3 | 92.0 |
| 9 | 95 | 120 | 3 | 91.0 |
| 10 | 195 | 185 | 3 | 18.8 |
| 11 | 168 | 203 | 3 | |

Figure 1:
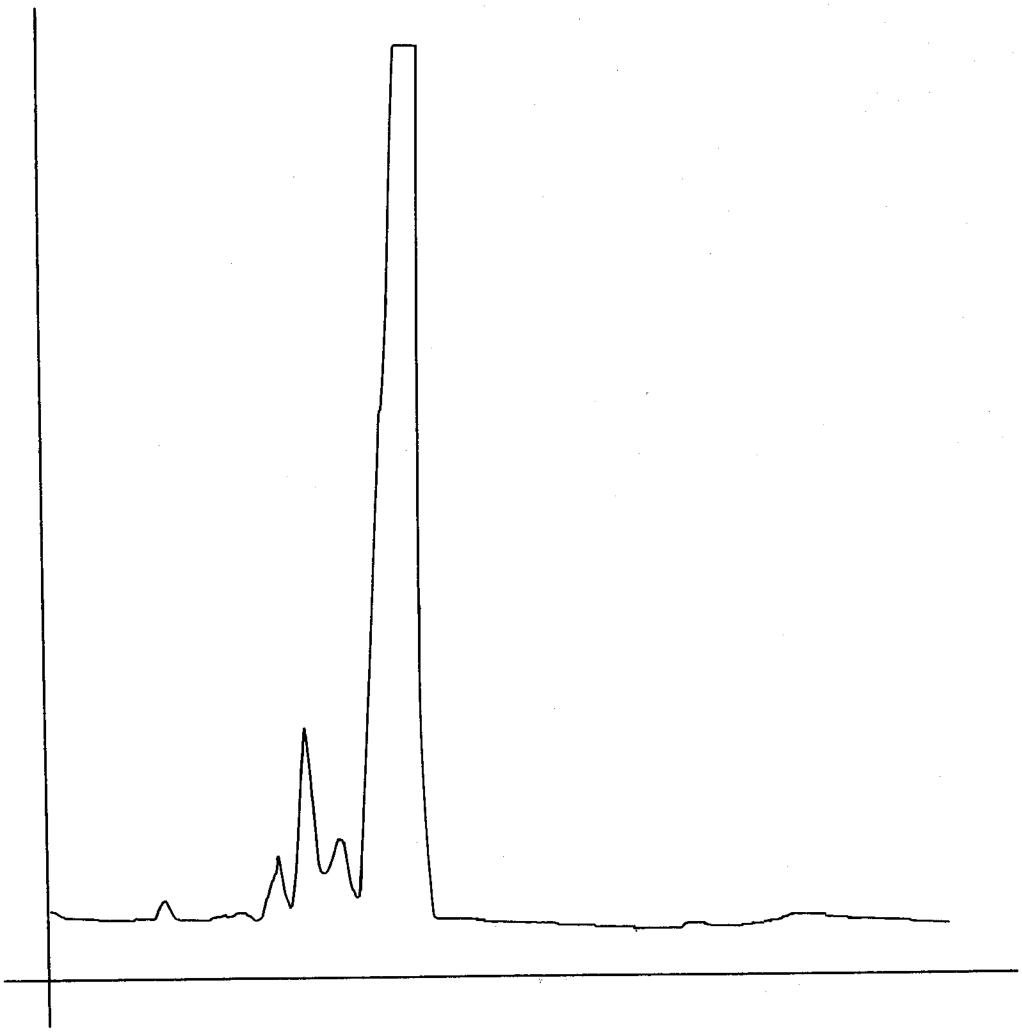
FIG. 1 is the GLC profile for fraction 7 of the distillation product of the reaction product of Example I containing the compounds having the structures.

FIG. 1 is the GLC profile for fraction 7. Analysis indicates that this fraction contains a major proportion (greater than 87%) of 4-cyclooctenyl formate and a minor proportion of bicyclooctanyl formate having the structure:

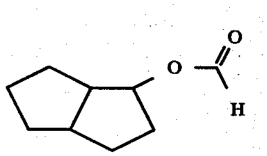

FIG. 2 is the NMR spectrum for fraction 5 of the foregoing distillation (Solvent: $CFCl_3$; Field Strength: 100 MHz).

FIG. 3 is the infra-red spectrum for fraction 5 of the foregoing distillation which contains a major proportion (greater than 78%) of 4-cyclooctenyl formate having the structure:

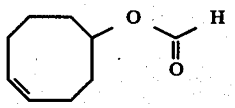

and a minor proportion of bicyclooctanyl formate having the structure:

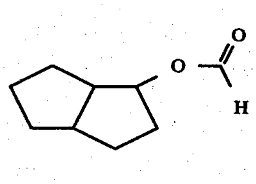

EXAMPLE II

PREPARATION OF COMPOSITION CONTAINING MAJOR PROPORTION OF 4-CYCLOOCTENYL METHYL CARBONATE

Reaction:

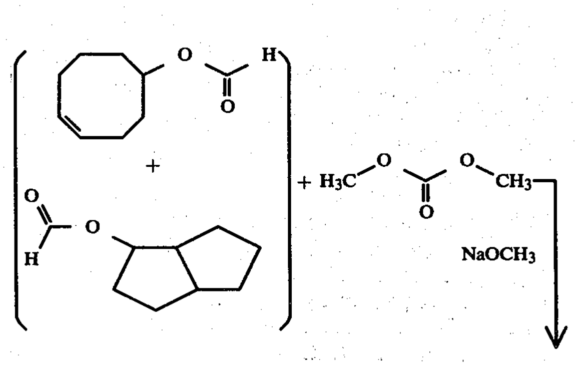

-continued

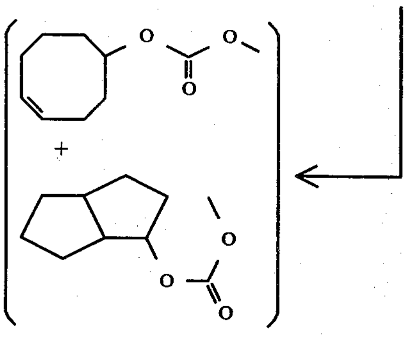

Into a 5-liter reaction flask equipped with heating mantle, stirrer, Bidwell trap, addition funnel, thermometer, reflux condenser and nitrogen blanket apparatus, are placed 2 liters (22.0 moles) of dimethyl carbonate and 81 grams (1.5 moles) of powdered sodium methoxide. The resulting mixture is heated to 65° C. and over a period of 4 hours while maintaining the temperature of the mixture at 60°-65° C., 1,719 grams (11.0 moles) of the composition containing a preponderance of 4-cyclooctenyl formate produced according to Example I (bulked distillation fractions 5,7 and 9) is added to the reaction mass while recovering methyl formate reaction product via the Bidwell trap. After addition is complete, the reaction mass is heated to 70° C. in order to remove the remaining methyl formate reaction product.

The reaction mass is then washed with two 500 ml portions of saturated sodium chloride and distilled on a 1' Goodloe column yielding the following fractions:

| Fraction Number | Vapor Temp. (°C.) | Liquid Temp. (°C.) | Pressure mm/Hg | Reflux Ratio | % of 4-cyclooctenyl Methyl Carbonate | Weight of Fraction (grams) |
|---|---|---|---|---|---|---|
| 1 | 48/64 | 89/95 | 1.8/3.0 | 4:1 | — | — |
| 2 | 62 | 97 | 1.4 | 4:1 | — | — |
| 3 | 70 | 100 | 2.6 | 4:1 | — | — |
| 4 | 77 | 100 | 1.4 | 4:1 | — | — |
| 5 | 72/87 | 95/98 | 2.3 | 9:1 | 78.0 | — |
| 6 | 80/92 | 112/105 | 6.5 | 4:1 | 93.0 | 52 |
| 7 | 92 | 107 | 4.6 | 4:1 | 97.0 | 88 |
| 8 | 92 | 107 | 4.0 | 4:1 | — | 112 |
| 9 | 86 | 110 | 3.0 | 4:1 | 98.0 | 119 |
| 10 | 86 | 113 | 3.0 | 4:1 | — | 113 |
| 11 | 86 | 115 | 3.0 | 4:1 | 98.8 | 130 |
| 12 | 86 | 116 | 3.0 | 4:1 | — | 99 |
| 13 | 86 | 118 | 3.0 | 4:1 | 99.8 | 101 |
| 14 | 86 | 120 | 3.0 | 4:1 | — | 65 |

Fractions 7-14 are bulked for the purpose of organoleptic evaluation.

FIG. 4 is the GLC profile for the reaction product prior to distillation. The numeral "1" represents the peak for methyl alcohol. The numeral "2" represents the peak for 4-cyclooctenyl formate that is not reacted. The reference numeral "3" represents the peak for the 4-cyclooctenyl methyl carbonate reaction product having the structure:

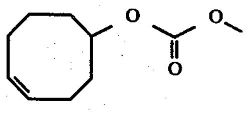

FIG. 5 is the GLC profile for fraction 13 of the foregoing distillation containing a major proportion of the compound having the structure:

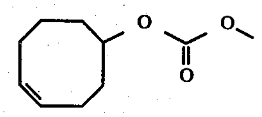

as well as a minor proportion of the compound having the structure:

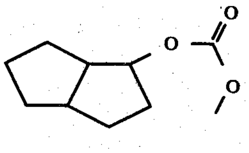

FIG. 6 is the NMR spectrum for fraction 13 of the foregoing distillation containing a major proportion of the compound having the structure:

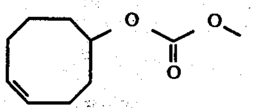

as well as a minor proportion of the compound having the structure:

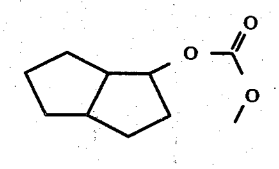

(Solvent: $CFCl_3$; Field Strength: 100 MHz).

FIG. 7 is the infra-red spectrum for fraction 13 of the foregoing distillation containing a major proportion of the compound having the structure:

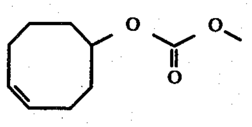

as well as a minor proportion of the compound having the structure:

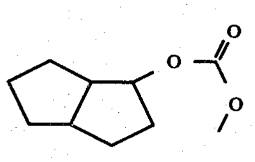

FIG. 8 is the GLC profile for fraction 7 of the foregoing distillation containing a major proportion of the compound having the structure:

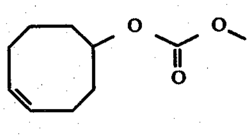

and a minor proportion of the compound having the structure:

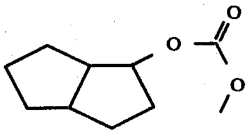

(ratio of compound having the structure:

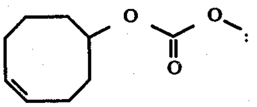

compound having the structure:

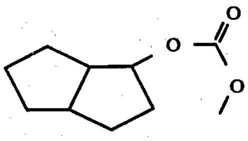

is 77:19).

FIG. 9 is the NMR spectrum for fraction 7 of the foregoing distillation containing the compound having the structure:

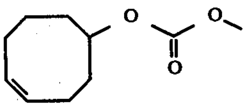

in major proportion and the compound having the structure:

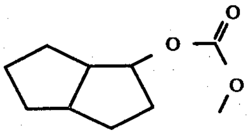

in minor proportion (Solvent: $CFCl_3$; Field Strength: 100 MHz).

FIG. 10 is the infra-red spectrum for fraction 7 of the foregoing distillation containing a major proportion of the compound having the structure:

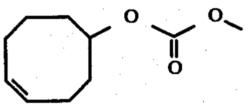

and a minor proportion of the compound having the structure:

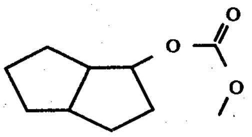

Bulked fractions 7–14 have a fruity (pear, banana), sweet, violet-like, green, cucumber aroma profile.

EXAMPLE III

PREPARATION OF 4-CYCLOOCTENYL ETHYL CARBONATE COMPOSITION

Reaction:

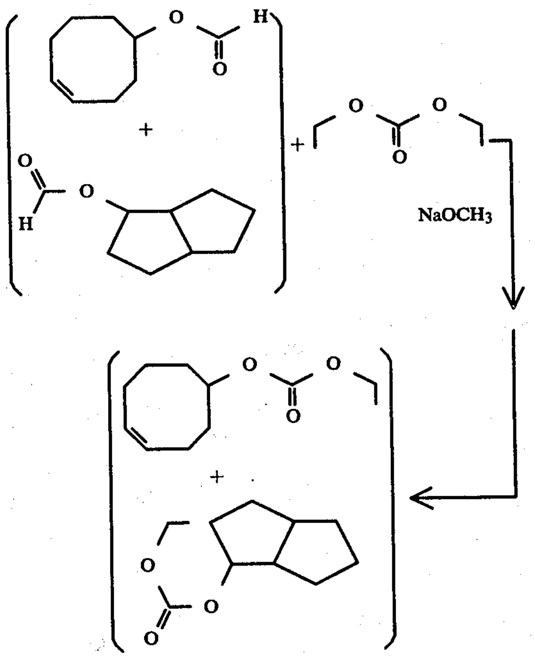

Into a 2 liter reaction flask equipped with heating mantle, stirrer, Bidwell water trap, reflux condenser, thermometer and nitrogen blanket apparatus is placed 1,000 ml (8.4 moles) of diethyl carbonate, and 25 grams (0.45 moles) of sodium methoxide. The resulting mixture is heated to 85° C. While maintaining the reaction mass at 85°–86° C. over a period of 1 hour, 695 grams (4.5 moles) of a composition containing a major proportion of 4-cyclooctenyl formate having the structure:

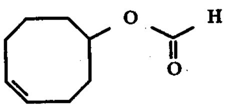

and a minor proportion of bicyclooctanyl formate having the structure:

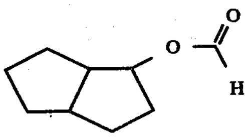

produced according to Example I, is added while removing ethyl formate reaction product from the reaction mass using the Bidwell trap. At the end of the 1 hour period, the reaction mass is stirred at a temperature of 85°-86° C. for an additional 1 hour.

The reaction mass is then added to 500 ml of saturated sodium chloride solution and stripped of the diethyl carbonate. The reaction mass is then distilled on a 1' Goodloe column yielding the following fractions:

| Fraction Number | Vapor Temp. (°C.) | Liquid Temp. (°C.) | Pressure mm/Hg | Reflux Ratio | % of 4-cyclooctenyl Ethyl Carbonate |
|---|---|---|---|---|---|
| 1 | 25/30 | 45/100 | 7/5 | 1:4/4:1 | — |
| 2 | 67 | 103 | 3.4 | 4:1 | — |
| 3 | 69 | 105 | 1.8 | 4:1 | — |
| 4 | 83 | 106 | 1.8 | 4:1 | 84 |
| 5 | 84 | 105 | 1.6 | 4:1 | 97 |
| 6 | 85 | 106 | 1.8 | 4:1 | — |
| 7 | 87 | 107 | 1.8 | 4:1 | — |
| 8 | 88 | 108 | 1.8 | 4:1 | 99 |
| 9 | 92 | 110 | 1.8 | 1:1 | — |
| 10 | 92 | 118 | 1.8 | 1:1 | — |
| 11 | 92 | 124 | 1.8 | 1:1 | 99 |
| 12 | 91 | 151 | 1.8 | 1:1 | 99 |

FIG. 11 is the GLC profile of the reaction mass prior to distillation and immediately subsequent to reaction (prior to "work-up") containing the compounds having the structure:

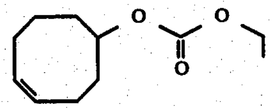

in major proportion and the compound having the structure:

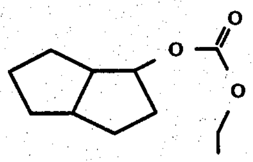

in minor proportion.

FIG. 12 is GLC profile for fraction 6 of the foregoing distillation containing the compound having the structure:

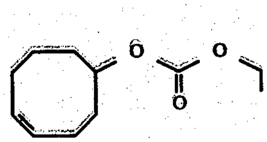

in major proportion and the compound having the structure:

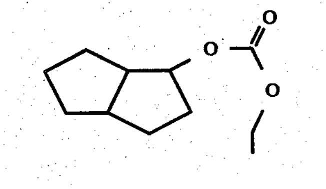

in minor proportion.

FIG. 13 is the infra-red spectrum for bulked fractions 9-12 of the foregoing distillation containing the compound having the structure:

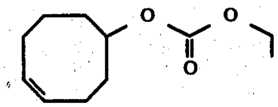

in major proportion and the compound having the structure:

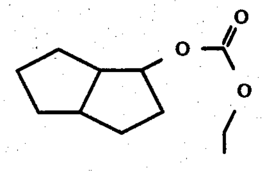

in minor proportion.

FIG. 14 is the NMR spectrum for bulked fractions 9-12 of the foregoing distillation (Solvent: $CFCl_3$; Field Strength: 100 MHz) containing the compound having the structure:

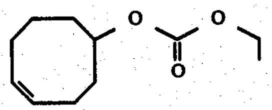

in major proportion and the compound having the structure:

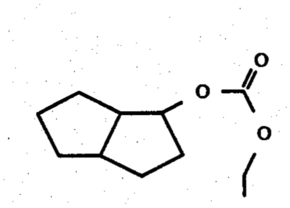

in minor proportion.

Bulked fractions 9-12 have a minty, strawberry-like aroma with tagette-like nuances on dry-out and a minty, strawberry-like, herbal aroma with tagette-like and birch tarlike undertones in general.

EXAMPLE IV

JASMINE PERFUME COMPOSITION

The following mixture is prepared:

| Ingredients | Parts by Weight |
|---|---|
| [Mixture containing high proportion of 4-cyclooctenyl methyl carbonate produced according to Example II, bulked fractions 7-14] | 230 |
| Benzyl acetate | 150 |
| Linalool | 60 |
| Linalyl acetate | 60 |
| Hydroxy citronellal | 60 |
| Elang oil | 40 |
| Methyl jasmonate | 25 |
| Benzyl salicylate | 15 |
| Geranyl acetate | 25 |
| n-undecanal | 25 |
| Para-cresyl phenyl acetate | 10 |
| Phenylethyl acetate | 20 |
| Phenylethyl alcohol | 50 |
| Indol | 20 |

-continued

| Ingredients | Parts by Weight |
|---|---|
| Coumarin | 12 |

The composition of matter containing a high proportion of 4-cyclooctenyl methyl carbonate produced according to Exmaple II (bulked fractions 7-14) adds an excellent fruity (pear, banana), natural, violet-like, green undertones to this jasmine formulation causing it to be much more natural-like and aesthetically pleasing.

EXAMPLE V

HERBAL FRAGRANCE FORMULATION PRODUCED USING THE PRODUCT PREPARED ACCORDING TO EXAMPLE III

| Ingredients | Parts by Weight |
|---|---|
| Amyl cinnamic aldehyde | 20 |
| Phenyl acetaldehyde dimethyl acetal | 4 |
| Thyme oil white | 8 |
| Sauge sclaree French | 8 |
| Galbanum oil | 4 |
| Juniper berry oil | 10 |
| Methyl octin carbonate | 4 |
| Linalyl acetate | 2 |
| Dihydro methyl jasmonate | 10 |
| [4-cyclooctenyl ethyl carbonate composition (containing minor proportion of compound having the structure: 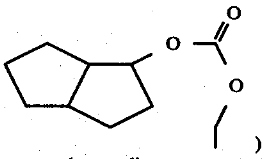 prepared according to Example III, bulked fractions 9-12] | 10 |

The composition of matter containing a high proportion of 4-cyclooctenyl ethyl carbonate prepared according to Example III adds a strong, minty, strawberry-like and herbal aroma with tagette-like and birch tar-like undertones to this herbal fragrance formulation causing it to be more "rain forest/natural-like".

EXAMPLE VI

PREPARATION OF COSMETIC POWDER COMPOSITIONS

Cosmetic powder compositions are prepared by mxing in a ball mill 100 grams of talcum powder with 0.25 grams of each of the substances set forth in Table I below. Each of the cosmetic powder compositions has an excellent aroma as described in Table I below.

TABLE I

| Substance | Aroma Description |
|---|---|
| Composition containing a high proportion of 4-cyclooctenyl methyl carbonate prepared according to Example II (bulked fractions 7-14). | A fruity (pear, banana-like) violet-like, cucumber aroma. |
| Fragrance formulation of Example IV. | A jasmine aroma having intense violet, green and fruity undertones. |
| Composition of matter containing a high proportion of 4-cyclooctenyl ethyl carbonate prepared according to Example III, bulked fractions 9-12, (containing a minor proportion of the compound having the structure: 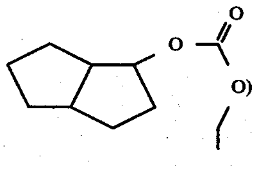 | A strawberry-like, herbal and minty aroma with tagette-like and birch tar-like undertones. |
| Perfume composition of Example V. | An intense, natural, rain forest, tropical aroma with minty, strawberry-like, herbal, tagette-like and birch tar-like nuances. |

EXAMPLE VII

PERFUMED LIQUID DETERGENTS

Concentrated liquid detergents (lysine salt of n-dodecylbenzene sulfonic acid as more specifically described in U.S. Pat. No. 3,948,818, issued Apr. 6, 1976 incorporated by reference herein) with aroma nuances as set forth in Table I of Example VI, are prepared containing 0.10%, 0.15%, 0.20%, 0.25%, 0.30% and 0.35% of the substance set forth in Table I of Example VI. They are prepared by adding and homogeneously mixing the appropriate quantity of substance set forth in Table I of Example VI in the liquid detergent. The detergents all possess excellent aromas as set forth in Table I of Example Vi, the intensity increasing with greater concentrations of substance as set forth in Table I of Example VI.

EXAMPLE VIII

PREPARATION OF COLOGNES AND HANDKERCHIEF PERFUMES

Compositions as set forth in Table I of Example VI are incorporated into colognes at concentrations of 2.0%, 2.5%, 3.0%, 3.5%, 4.0%, 4.5% and 5.0% in 80%, 85%, 90% and 95% aqueous food grade ethanol solutions; and into handkerchief perfumes at concentrations of 15%, 20%, 25% and 30% (in 80%, 85%, 90% and 95% aqueous food grade ethanol solutions). Distinctive and definitive fragrances as set forth in Table I of Example VI are imparted to the colognes and to the handkerchief perfumes at all levels indicated.

EXAMPLE IX

PREPARATION OF SOAP COMPOSITIONS

One hundred grams of soap chips (per sample) (IVORY ®. produced by the Procter & Gamble Company of Cincinnati, Ohio), are each mixed with one gram samples of substances as set forth in Table I of Example VI until homogeneous compositions are obtained. In each of the cases, the homogeneous compositions are heated under 8 atmospheres, pressure at 180° C. for a period of three hours and the resulting liquids are placed into soap molds. The resulting soap cakes, on cooling, manifest aromas as set forth in Table I of Example VI.

EXAMPLE X

PREPARATION OF SOLID DETERGENT COMPOSITIONS

Detergents are prepared using the following ingredients according to Example I of Canadian Pat. No. 1,007,948 (incorporated by reference herein):

| Ingredient | Percent by Weight |
|---|---|
| Neodol ® 45-11 (a $C_{14}$-$C_{15}$ alcohol ethoxylated with 11 moles of ethylene oxide) | 12 |
| Sodium carbonate | 55 |
| Sodium citrate | 20 |
| Sodium sulfate, water brighteners | q.s. |

This detergent is a phosphate-free detergent. Samples of 100 grams each of this detergent are admixed with 0.10, 0.15, 0.20 and 0.25 grams of each of the substances as set forth in Table I of Example VI. Each of the detergent samples has an excellent aroma as indicated in Table I of Example VI.

EXAMPLE XI

Utilizing the procedure of Example I at column 15 of U.S. Pat. No. 3,632,396 (the disclosure of which is incorporated herein by reference), nonwoven cloth substrates useful as drier-added fabric softening articles of manufacture are prepared wherein the substrate, the substrate coating, the outer coating and the perfuming material are as follows:

1. A water "dissolvable" paper ("Dissolvo Paper");
2. Adogen 448 (m.p. about 140° F.) as the substrate coating; and
3. An outer coating having the following formulation (m.p. about 150° F.):
   57% $C_{20-22}$ HAPS
   22% isopropyl alcohol
   20% antistatic agent
   1% of one of the substances as set forth in Table I of Example VI.

Fabric softening compositions prepared according to Example I at column 15 of U.S. Pat. No. 3,632,396 having aroma characteristics as set forth in Table I of Example VI supra, consist of a substrate coating having a weight of about 3 grams per 100 square inches of substrate; a first coating located directly on the substrate coating consisting of about 1.85 grams per 100 square inches of substrate; and an outer coating coated on the first coating consisting of about 1.4 grams per 100 square inches of substrate. One of the substances of Table I of Example VI is admixed in each case with the outer coating mixture, thereby providing a total aromatized outer coating weight ratio to substrate of about 0.5:1 by weight of the substrate. The aroma characteristics are imparted in a pleasant manner to the head space in a drier on operation thereof in each case using said drier-added fabric softener non-woven fabrics and these aroma characteristics are described in Table I of Example VI, supra.

EXAMPLE XII

HAIR SPRAY FORMULATIONS

The following hair spray formulation is prepared by first dissolving PVP/VA E-735 copolymer manufactured by the GAF Corporation of 140 West 51st Street, New York, N.Y. in 91.62 grams of 95% food grade ethanol. 8.0 grams of the polymer is dissolved in the alcohol. The following ingredients are added to the PVP/VA alcoholic solution:

| | |
|---|---|
| Dioctyl sebacate | 0.05 weight percent |
| Benzyl alcohol | 0.10 weight percent |
| Dow Corning 473 fluid (prepared by the Dow Corning Corporation) | 0.10 weight percent |
| Tween 20 surfactant (prepared by ICI America Corporation) | 0.03 weight percent |
| One of the perfumery substances as set forth in Table I of Example VI | 0.10 weight percent |

The perfuming substances as set forth in Table I of Example VI add aroma characteristics as set forth in Table I of Example VI which are rather intense and aesthetically pleasing to the users of the soft-feel, good-hold pump hair sprays.

EXAMPLE XIII

CONDITIONING SHAMPOOS

Monamid CMA (prepared by the Mona Industries Company) (3.0 weight percent) is melted with 2.0 weight percent coconut fatty acid (prepared by Procter & Gamble Company of Cincinnati, Ohio); 1.0 weight percent ethylene glycol distearate (prepared by the Armak Corporation) and triethanolamine (a product of Union Carbide Corporation) (1.4 weight percent). The resulting melt is admixed with Stepanol WAT produced by the Stepan Chemical Company (35.0 weight percent). The resulting mixture is heated to 60° C. and mixed until a clear solution is obtained (at 60° C.). This material is "Composition A".

Gafquat® 755 N polymer (manufactured by GAF Corporation of 140 West 51st Street, New York, N.Y.) (5.0 weight percent is admixed with 0.1 weight percent sodium sulfite and 1.4 weight percent polyethylene glycol 6000 distearate produced by Armak Corporation. This material is "Composition B".

The resulting "Composition A" and "Composition B" are then mixed in a 50:50 weight ratio of A:B and cooled to 45° C. and 0.3 weight percent of perfuming substance as set forth in Table I of Example VI is added to the mixture. The resulting mixture is cooled to 40° C. and blending is carried out for an additional one hour in each case. At the end of this blending period, the resulting material has a pleasant fragrance as indicated in Table I of Example VI.

What is claimed is:

1. A process for producing a composition containing a major proportion of 4-cyclooctenyl alkyl carbonate comprising the steps of:

(i) refluxing a mixture of 1,5-cyclooctadiene and formic acid to prepare a mixture of 4-cyclooctenyl formate having the structure:

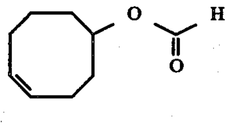

and bicyclooctanyl formate having the structure:

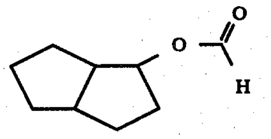

(ii) reacting the resulting mixture of 4-cyclooctenyl formate and bicyclooctanyl formate with a dialkyl carbonate defined according to the structure:

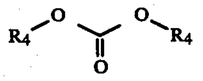

wherein $R_4$ is methyl or ethyl in the presence of an alkali metal alkoxide catalyst in order to produce a mixture containing a major proportion of compounds defined according to the structure:

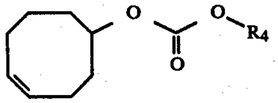

and a minor proportion of the compound defined according to the structure:

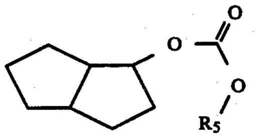

wherein $R_4$ and $R_5$ are the same and each represent methyl or ethyl.

2. The product produced according to the process of claim 1.

3. A process for augmenting or enhancing the aroma of consumable material selected from the group consisting of perfume compositions and, colognes comprising the step of intimately admixing with a perfume composition base, a cologne base an aroma augmenting or enhancing quantity of at least one 4-cyclooctenyl alkyl carbonate defined according to the structure:

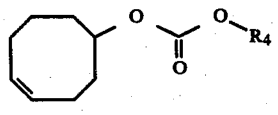

wherein $R_4$ represents an alkyl group selected from the group consisting of methyl and ethyl.

4. A process for augmenting or enhancing the aroma of a consumable material selected from the group consisting of perfume compositions and colognes comprising the step of intimately admixing with a perfume composition base or a cologne base an aroma augmenting or enhancing quantity of a product produced according to a process comprising the steps of:

(i) refluxing a mixture of 1,5-cyclooctadiene and formic acid to prepare a mixture of 4-cyclooctenyl formate having the structure:

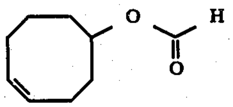

and bicyclooctanyl formate having the structure:

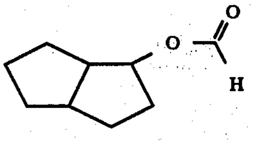

(ii) reacting the resulting mixture of 4-cyclooctenyl formate and bicyclooctanyl formate with a dialkyl carbonate defined according to the structure:

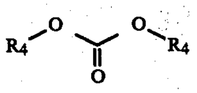

wherein $R_4$ is methyl or ethyl in the presence of an alkali metal alkoxide catalyst in order to produce a mixture containing a major proportion of compounds defined according to the structure:

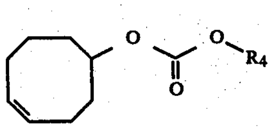

and a minor proportion of the compound defined according to the structure:

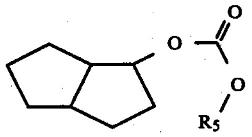

wherein $R_4$ and $R_5$ are the same and each represent methyl or ethyl.

* * * * *